(12) United States Patent    (10) Patent No.:    US 12,622,994 B2
Shatalov et al.    (45) Date of Patent:    May 12, 2026

(54) LIGHT FIXTURE WITH UV DISINFECTION

(71) Applicant: APOGEE LIGHTING HOLDINGS, LLC, Deer Park, NY (US)

(72) Inventors: Maxim S. Shatalov, Mount Sinai, NY (US); Michael Handerhan, New York, NY (US)

(73) Assignee: APOGEE LIGHTING HOLDINGS, LLC, Deer Park, NY (US)

( * ) Notice:    Subject to any disclaimer, the term of this patent is extended or adjusted under 35 U.S.C. 154(b) by 1241 days.

(21) Appl. No.: 17/504,972

(22) Filed:    Oct. 19, 2021

(65)    Prior Publication Data

US 2022/0118148 A1    Apr. 21, 2022

Related U.S. Application Data

(60) Provisional application No. 63/115,411, filed on Nov. 18, 2020, provisional application No. 63/093,434, filed on Oct. 19, 2020.

(51) Int. Cl.
| *A61L 9/20* | (2006.01) |
| *A61L 2/00* | (2006.01) |
| *A61L 2/022* | (2026.01) |
| *A61L 2/10* | (2006.01) |
| *A61L 2/24* | (2006.01) |
| *B01D 39/16* | (2006.01) |

(Continued)

(52) U.S. Cl.
CPC .............. *A61L 9/20* (2013.01); *A61L 2/0017* (2013.01); *A61L 2/0047* (2013.01); *A61L 2/022* (2013.01); *A61L 2/10* (2013.01); *A61L 2/24* (2013.01); *B01D 39/16* (2013.01); *F21S 8/06* (2013.01); *F21V 7/0008* (2013.01); *F21V 33/0096* (2013.01); *A61L 2202/11* (2013.01); *A61L 2202/14* (2013.01); *A61L 2202/15* (2013.01); *A61L 2202/25* (2013.01); *A61L 2209/11* (2013.01); *A61L 2209/12* (2013.01); *A61L 2209/14* (2013.01); *A61L 2209/15* (2013.01); *B01D 2201/184* (2013.01); *B01D 2257/91* (2013.01); *B01D 2321/343* (2013.01); *F21Y 2115/10* (2016.08)

(58) Field of Classification Search
CPC .................................. A61L 9/20; A61L 9/205
See application file for complete search history.

(56)    References Cited

U.S. PATENT DOCUMENTS

| 5,656,242 A | 8/1997 | Morrow et al. |
| 5,874,701 A | 2/1999 | Watanabe et al. |

(Continued)

FOREIGN PATENT DOCUMENTS

| CN | 2464308 Y | 12/2001 |
| KR | 20010092279 | 10/2001 |

(Continued)

OTHER PUBLICATIONS

International Search Report issued in PCT Application No. PCT/US2021/055617, Dated Feb. 14, 2022, pp. 1-12.

*Primary Examiner* — Donald R Spamer
(74) *Attorney, Agent, or Firm* — Tutunjian & Bitetto, P.C.

(57)    ABSTRACT

A light fixture includes a housing forming a cavity to permit airflow therethrough. A filter is disposed within the airflow of the cavity. An ultraviolet light emitting diode is disposed within the cavity and is directed to concurrently treat the airflow and the filter to destroy biomaterial therein.

26 Claims, 39 Drawing Sheets

(51) Int. Cl.
    *F21S 8/06*            (2006.01)
    *F21V 7/00*            (2006.01)
    *F21V 33/00*        (2006.01)
    *F21Y 115/10*       (2016.01)

(56)             References Cited

U.S. PATENT DOCUMENTS

| | | | |
|---|---|---|---|
| 5,891,399 A * | 4/1999 | Owesen | A61L 9/20 |
| | | | 422/121 |
| 6,139,803 A | 10/2000 | Watanabe et al. | |
| 6,787,782 B1 * | 9/2004 | Krosney | A61L 9/20 |
| | | | 250/435 |
| 6,861,787 B2 | 3/2005 | Matsuda et al. | |
| 7,703,951 B2 | 4/2010 | Piepgras et al. | |
| 8,080,203 B2 * | 12/2011 | First | A61L 9/20 |
| | | | 422/24 |
| 8,231,256 B1 | 7/2012 | Coleman et al. | |
| 8,362,713 B2 | 1/2013 | Recker et al. | |
| 8,829,799 B2 | 9/2014 | Recker et al. | |
| 9,295,931 B2 | 3/2016 | Mori et al. | |
| 9,358,313 B2 | 6/2016 | Deal | |
| 9,370,600 B1 | 6/2016 | DuPuis et al. | |
| 9,642,358 B2 | 5/2017 | Cai et al. | |
| 9,699,869 B2 | 7/2017 | Holland et al. | |
| 9,724,440 B2 | 8/2017 | Bugenske et al. | |
| 10,960,098 B2 | 3/2021 | Zarcone et al. | |
| 2002/0031460 A1 | 3/2002 | Kulp | |
| 2002/0168305 A1 | 11/2002 | Morrow et al. | |
| 2003/0019738 A1 * | 1/2003 | Reisfeld | B01D 53/86 |
| | | | 422/186 |
| 2003/0039576 A1 | 2/2003 | Hall | |
| 2005/0191205 A1 * | 9/2005 | Uslenghi | A61L 9/20 |
| | | | 422/4 |
| 2007/0023710 A1 * | 2/2007 | Tom | A61L 2/10 |
| | | | 422/62 |
| 2007/0053188 A1 | 3/2007 | New et al. | |
| 2008/0180935 A1 | 7/2008 | Burdeen et al. | |
| 2009/0004066 A1 | 1/2009 | Cheng | |
| 2009/0133582 A1 * | 5/2009 | Snowball | A61L 9/20 |
| | | | 96/224 |
| 2009/0154148 A1 | 6/2009 | Meyer et al. | |
| 2011/0001060 A1 | 1/2011 | Welker | |
| 2012/0199005 A1 | 8/2012 | Koji et al. | |
| 2013/0291735 A1 | 11/2013 | Livchak et al. | |
| 2015/0330587 A1 | 11/2015 | Lax et al. | |
| 2017/0003015 A1 | 1/2017 | Schreiber | |
| 2017/0238401 A1 | 8/2017 | Sadwick et al. | |
| 2017/0276205 A1 | 9/2017 | Ogawa et al. | |
| 2017/0307242 A1 | 10/2017 | Handsaker et al. | |
| 2017/0321877 A1 | 11/2017 | Polidoro | |
| 2018/0172258 A1 | 6/2018 | Schreiber | |
| 2018/0299117 A1 | 10/2018 | Min | |
| 2019/0113219 A1 | 4/2019 | Niemiec et al. | |
| 2019/0257314 A1 | 8/2019 | Niemiec et al. | |
| 2019/0292315 A1 | 9/2019 | Niemiec et al. | |
| 2019/0358584 A1 | 11/2019 | Pendo et al. | |
| 2019/0360686 A1 | 11/2019 | Pendo et al. | |
| 2020/0009286 A1 * | 1/2020 | Zarcone | H05B 47/19 |

FOREIGN PATENT DOCUMENTS

| | | | |
|---|---|---|---|
| KR | 20180125833 A | 11/2018 | |
| WO | 2016099508 A1 | 6/2016 | |

* cited by examiner

613 - Vector connecting emitting point with top portion of fixture

625

613

Elongated housing for elongated
distribution

626

613

515

1013

1015

519

1011A

1011B

505

1311 - Reference Reflector

1312 - No bent reflector part

1313 - No reflector

1311 - Reference Reflector          1312 - No bent reflector part          1313 - No reflector UV LED boards with 20 deg 2θ beam angle – side wall Same reflector configuration - reference No flat reflector part

FIG. 22

UV LED boards with 20 deg 2θ beam angle - ceiling

No flat reflector part

Same reflector configuration - reference

UV LED boards with 20 deg 2θ beam angle - ceiling

No flat reflector part

Same reflector configuration - reference

UV LED boards with 20 deg 2θ beam angle - ceiling 50 deg angle for slanted reflector Reference – 20 deg angle for slanted reflector UV LED boards with 40 deg 2θ beam angle - ceiling 50 deg angle for slanted reflector Reference – 20 deg angle for slanted reflector UV LED boards with 40 deg 2θ beam angle - ceiling Reference – 20 deg angle for slanted reflector 50 deg angle for slanted reflector UV LED boards with 40 deg 2θ beam angle - ceiling 55 deg angle for slanted reflector Reference – 20 deg angle for slanted reflector

UV LED boards with 40 deg 2θ beam angle – ceiling 55 deg angle for slanted reflector Reference – 20 deg angle for slanted reflector UV LED boards with 40 deg 2θ beam angle - ceiling 60 deg angle for slanted reflector Reference – 20 deg angle for slanted reflector UV LED boards with 40 deg 2θ beam angle - ceiling 60 deg angle for slanted reflector Reference – 20 deg angle for slanted reflector UV LED boards with 60 deg 2θ beam angle - ceiling 60 deg angle for slanted reflector Reference −20 deg angle for slanted reflector

LIGHT FIXTURE WITH UV DISINFECTION

RELATED APPLICATION INFORMATION

This application claims priority to U.S. Provisional Application No. 63/093,434, filed on Oct. 19, 2020, and to U.S. Provisional Application No. 63/115,411, filed on Nov. 18, 2020, both incorporated herein by reference in their entirety.

TECHNICAL FIELD

The present disclosure generally relates to disinfection and sanitization, and more particularly, to the disinfection and sanitization of air from ultraviolet light source incorporated into the light fixture.

BACKGROUND

Ultraviolet disinfection systems are known and have a successful history of use in the reduction of viable concentrations of bacteria, viruses, protozoa, and fungi. The core unit of these ultraviolet systems is/are a source(s) of ultraviolet radiation having wavelength(s) close to the absorption peaks of biologically significant molecules of DNA, RNA, and proteins. The system can disinfect a medium, such as water, air, or surface, to a safe condition as long as the irradiance from the ultraviolet source and the exposure time are sufficient to create a high enough disinfection dose to modify and/or destroy the internal molecular structure of the pathogens. The vast majority of known ultraviolet disinfection systems typically use mercury lamps, xenon arc lamps, excimer lamps, or UV light emitting diodes (LED) as a source of ultraviolet radiation.

Low-pressure and medium-pressure mercury lamps provide a linear spectrum of radiation with wavelengths that are in the relative vicinity to a DNA absorption spectrum. UV LEDs provide a relatively narrow spectrum of radiation of approximately 5 nm to approximately 20 nm, such that the peak of the spectrum of radiation can be further tuned to have wavelength values in the vicinity or close to one of peak DNA absorption wavelength values. UV LED light sources frequently provide the flexibility of design and features lacking in mercury lamps, xenon arc lamps, and excimer lamps. Ultraviolet light emitting sources provide a convenient and effective way for the disinfection of surfaces. However, installing a new ultraviolet light emitting system in common high occupancy facilities such as classrooms, office conference rooms, medical facility lobbies, and restaurants may have high associated costs related to mounting ultraviolet sources at different locations within a facility, providing electrical wiring and power to such ultraviolet sources and providing means for controlling these sources.

Accordingly, there is a need to reduce costs associated with installing these sources by providing ways to retrofit existing light emitting sources with ultraviolet light emitting capability. The present disclosure provides systems and methods that address various problems associated with the deployment of ultraviolet light emitting sources for the disinfection of surfaces.

SUMMARY

Consistent with a disclosed embodiment, a light fixture is provided. The light fixture may include an ultraviolet radiation source comprising at least one ultraviolet light emitting diode configured to generate ultraviolet radiation. Further, the light fixture may include a housing that further includes a cavity through which the airflow is directed by the fan. The cavity can include at least one air filter. The at least one air filter can include a HEPA equivalent filter. The at least one air filter can include a dust prefilter and/or a porous PTFE filter. The at least one air filter can be irradiated by ultraviolet radiation. The housing further comprises ultraviolet light emitting diodes positioned within the cavity to irradiate the air filter.

Consistent with a disclosed embodiment, a light fixture is provided. The light fixture may include an ultraviolet radiation source comprising at least one ultraviolet light emitting diode configured to generate ultraviolet radiation. Further, the light fixture may include a reflector being reflective (but not transparent) to the ultraviolet radiation, the reflector having a top surface, the top surface comprising a distant region and an adjacent region, wherein at least a portion of the adjacent region is located close to and below the ultraviolet radiation source, and wherein the distant region comprises a rim located above a top-most emitting point of the ultraviolet radiation source, the reflector having at least partially reflective surface with reflectivity of at least 80% in the ultraviolet region, the reflector having a visible illumination light source in proximity to a bottom surface.

Consistent with another disclosed embodiment, a light fixture is provided. The light fixture may include an ultraviolet radiation source comprising at least one ultraviolet light emitting diode configured to generate germicidal ultraviolet radiation. Further, the light fixture may include a reflector being not transparent to the ultraviolet radiation, the reflector comprising a top surface, the top surface including a first surface adjacent to the source and a second surface adjacent to the first surface, wherein every point of the second surface is located either at the same level or above every point of the first surface, wherein the reflector is configured to reflect the ultraviolet radiation above the reflector, in a volume containing air. Also, the light fixture may include a fan configured to direct the air exposed to the ultraviolet radiation from the volume towards a region located underneath the reflector, wherein an operation of the fan is selected such that an airflow resulted from the operation of the fan is such that at least some of the air located in the volume acquires a target dose of the ultraviolet radiation.

Consistent with another disclosed embodiment, a system of light fixtures is provided. Each light fixture may include an ultraviolet radiation source comprising at least one ultraviolet light emitting diode configured to generate ultraviolet radiation, and a reflector being reflective (but not transparent) to the ultraviolet radiation, the reflector having a top surface, the top surface comprising a distant region and an adjacent region, wherein at least a portion of the adjacent region is located close to and below the ultraviolet radiation source, and wherein the distant region comprises a rim located above a top-most emitting point of the ultraviolet radiation source, the reflector having at least partially reflective surface with reflectivity of at least 70% in the ultraviolet region, the reflector having a visible illumination light source in proximity to a bottom surface. Further, the light fixture may include a controller for controlling aspects of operation of any one of the plurality of light fixtures, wherein the controller is configured to control at least one of an intensity of radiation of the at least one light emitting diode, or an operation of the fan.

Consistent with another disclosed embodiment, a light fixture is provided. The light fixture may include an ultraviolet radiation source comprising at least one ultraviolet light emitting diode configured to generate ultraviolet radiation. Further, the light fixture may include a reflector being not transparent to the ultraviolet radiation, the reflector comprising a top surface, the top surface including a first surface adjacent to the source and a second surface adjacent to the first surface, wherein every point of the second surface is located either at the same level or above every point of the first surface, wherein the second surface includes a rim comprising a closed curve with points of the rim being higher than any points of the first or the second surface, or any emitting point of the ultraviolet radiation source.

In another embodiment, a light fixture includes an ultraviolet radiation source having at least one ultraviolet light emitting diode configured to generate an ultraviolet radiation, a reflector being not transparent to the ultraviolet radiation, the reflector has a top surface, the top surface including a first surface adjacent to the source and a second surface adjacent to the first surface, wherein every point of the second surface is located either at the same level or above every point of the first surface, wherein the second surface includes a rim comprising a closed curve with points of the rim being higher than any points of the first or the second surface, or any emitting point of the ultraviolet radiation source. The reflector is configured to expose an air region to a target dose of the ultraviolet radiation. A fan is configured to direct the air exposed to the ultraviolet radiation within the air region towards a region located underneath the reflector, wherein exposing the air region to the target dose of the ultraviolet radiation is achieved by selecting a fan speed and an intensity of the ultraviolet radiation within the air region.

In other embodiments, at least one ultraviolet light emitting diode emits light with an angular distribution having a half-width at half-maximum angle in a range of 10 to 60 degrees. A housing having a length, height and width dimensions, can include a left and a right side, a bottom side, and a top side, wherein the left and the right side have an area of the length times the height a first set of light emitting diodes adjacent to the left side of the housing and a second set of light emitting diodes adjacent to the right side of the housing. In one embodiment, the length of the housing is at least five times larger than the height or the width of the housing. The reflector may be adjacent to the bottom side of the housing. The light fixture can be suspended from a ceiling of a room by an element attached to the top side of the housing. The housing can include a fan configured to receive air from the top side of the housing and direct a flow of air towards a floor of a room. The reflector can be configured to prevent light emitted from the at least one ultraviolet radiation source to illuminate any portion of a room, in which the light fixture is located below the rim of the reflector. The light fixture can include a filter disposed at an inlet of the cavity and within the volume of air such that the filter is exposed to radiation from the ultraviolet radiation source during operation.

A controller can be employed to control an intensity of radiation of at least one light emitting diode or an operation of a fan. The controller can be configured to control the intensity of radiation of the at least one light emitting diode, or an operation of the fan based on a dimension of a room in which the light fixture is installed. The controller can be configured to control the intensity of radiation of the at least one light emitting diode, or an operation of the fan based on a number of people present in a room in which the light fixture is installed. The controller can be configured to control the intensity of radiation of the at least one light emitting diode, or an operation of the fan based on a number of people present in a room in which the light fixture is installed.

The light fixture can be configured to have airflow in a vicinity of the fixture, wherein a moving parcel of air in a volume above the reflector receives a target radiational dose prior to exiting the volume, wherein the volume has dimensions of a length, a height, and a width, wherein the length is at least a length of the light fixture, and a width is at least a foot, and a height is a smallest one of a foot or a distance between the light fixture and a ceiling. A first distance from a rim of a reflector to the at least one ultraviolet light emitting diode can include a distribution of ultraviolet radiation above the light fixture such that a volume having a highest radiational intensity is located in at least one region positioned between one and five first distances from the at least one ultraviolet light emitting diode. The volume can have a highest radiational intensity about as long as the light fixture. The intensity of the ultraviolet radiation within the air region can be determined by an ultraviolet intensity emitted by ultraviolet radiation sources and angular distribution of the ultraviolet intensity emitted by ultraviolet radiation sources. The intensity of the ultraviolet radiation within the air region can be based on a shape of the reflector.

The present embodiments provide systems and methods for upper room and air disinfection. The system includes a light fixture which includes an ultraviolet radiation source comprising at least one ultraviolet light emitting diode configured to generate ultraviolet radiation. The light fixture also includes a reflector being not transparent to the ultraviolet radiation, the reflector has a top surface, the top surface comprising a distant region and an adjacent region, wherein at least a portion of the adjacent region is located close to and below the ultraviolet radiation source, and wherein the distant region comprises a rim located above a top-most emitting point of the ultraviolet radiation source, the reflector having at least partially reflective surface with reflectivity of at least eighty percent in the ultraviolet region, the reflector having a visible illumination light source in proximity to a bottom surface. The light fixture includes filters, fan and at least one ultraviolet radiation source comprising at least one ultraviolet light emitting diode configured to generate ultraviolet radiation.

The foregoing general description and the following detailed description are exemplary and explanatory only and are not restrictive of the claims.

BRIEF DESCRIPTION OF THE DRAWINGS

Embodiments and various aspects of the present disclosure are illustrated in the following detailed description and the accompanying figures. Various features shown in the figures are not drawn to scale.

Figure 22:
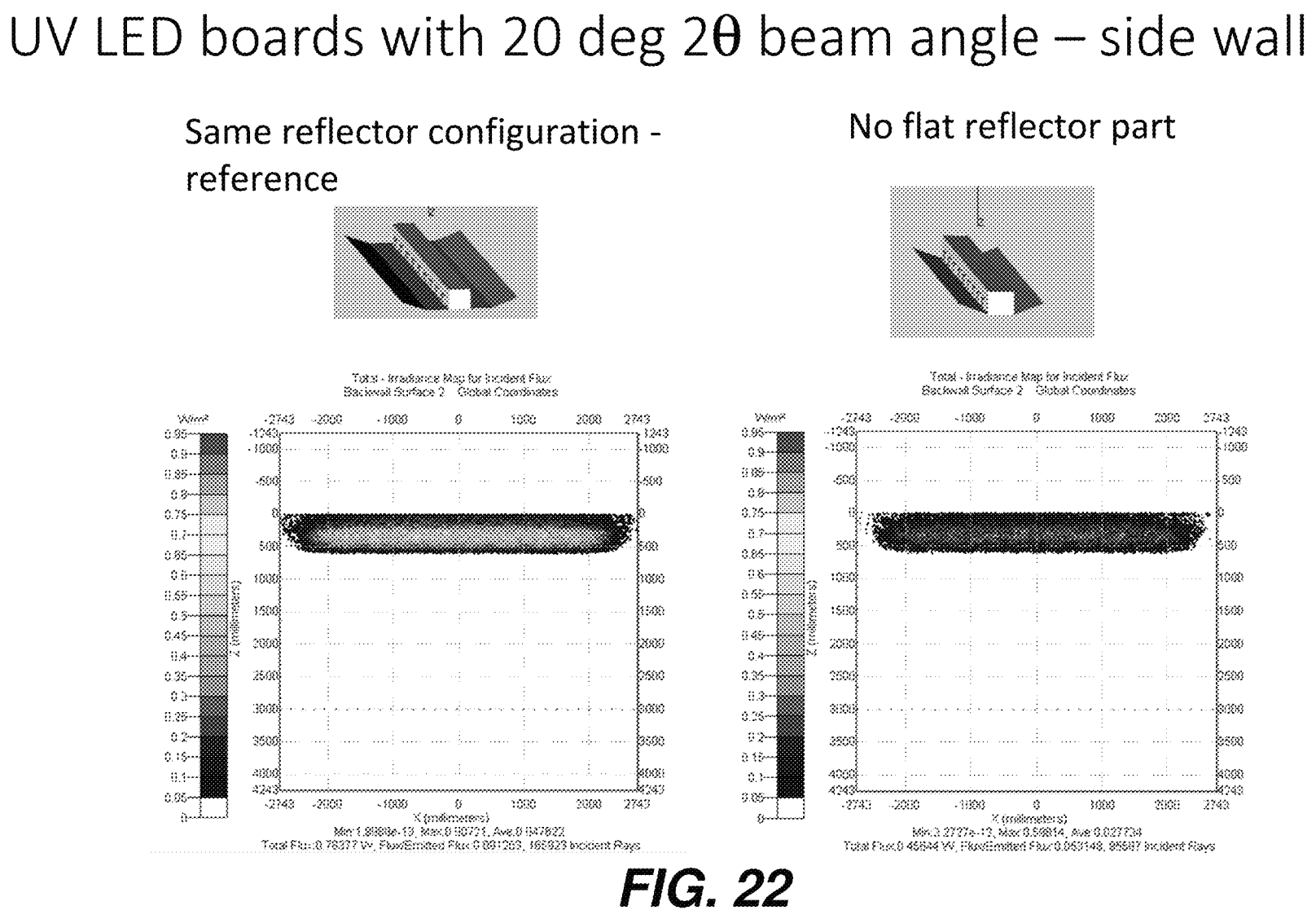

FIG. 22 shows another example distribution of ultraviolet light intensity over various surfaces, where the ultraviolet light is emitted by ultraviolet light sources with different angular distribution of light intensity, consistent with disclosed embodiments.

DETAILED DESCRIPTION OF PREFERRED EMBODIMENTS

Reference will now be made in detail to example embodiments, including those illustrated in the accompanying drawings. The following description refers to the accompanying drawings in which the same numbers in different drawings represent the same or similar elements unless otherwise represented. The implementations set forth in the following description of the embodiments do not represent all possible implementations consistent with the invention. Instead, they are merely examples of systems and methods consistent with aspects related to the invention as recited in the appended claims. Particular aspects of the present disclosure are described in greater detail below.

Figure 1:
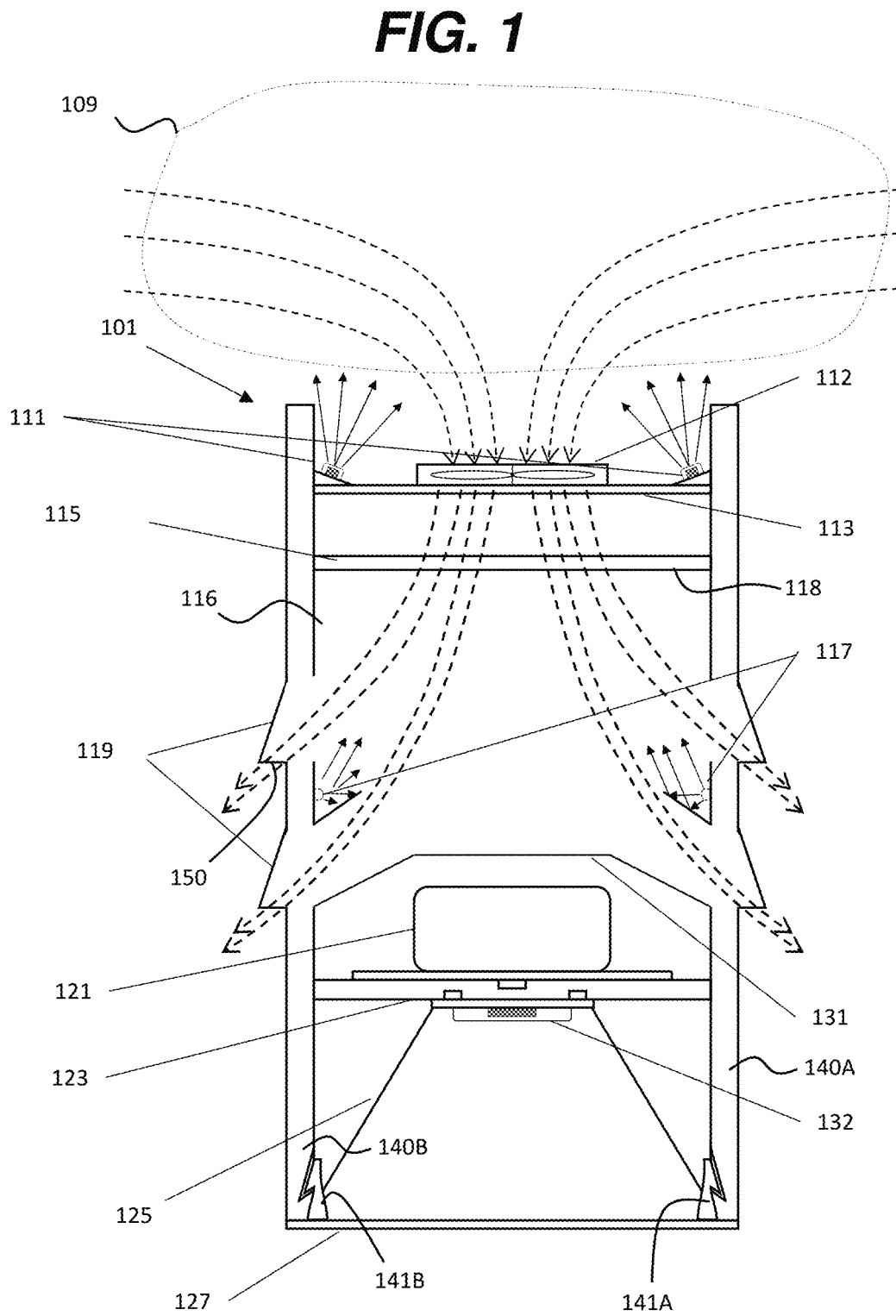
FIG. 1 shows an example light fixture with ultraviolet radiation sources, a fan and an air filter(s), consistent with disclosed embodiments.
Figure 2:
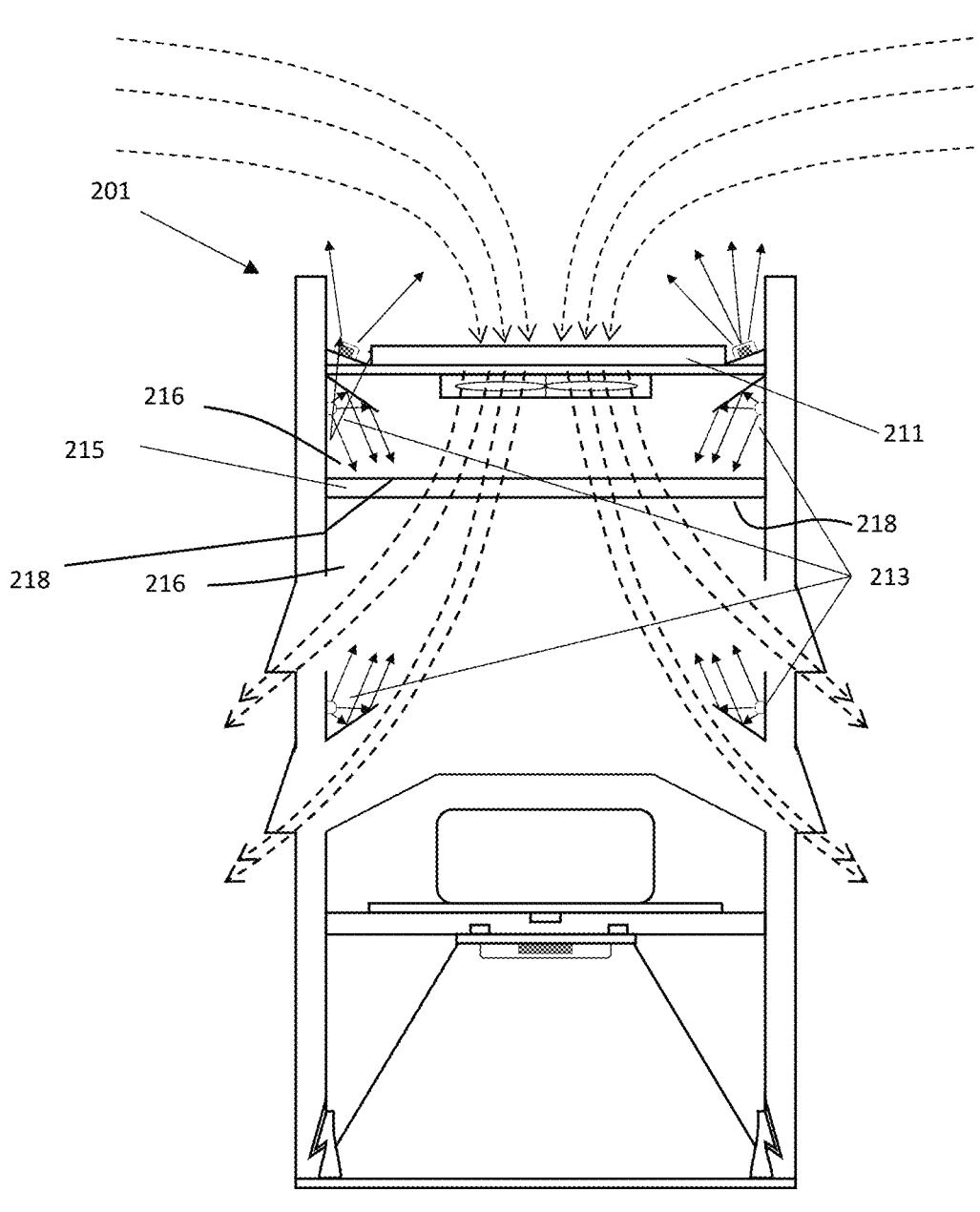
FIG. 2 shows an example light fixture with ultraviolet radiation sources, a fan and an air filter(s), consistent with disclosed embodiments.
Figure 3:
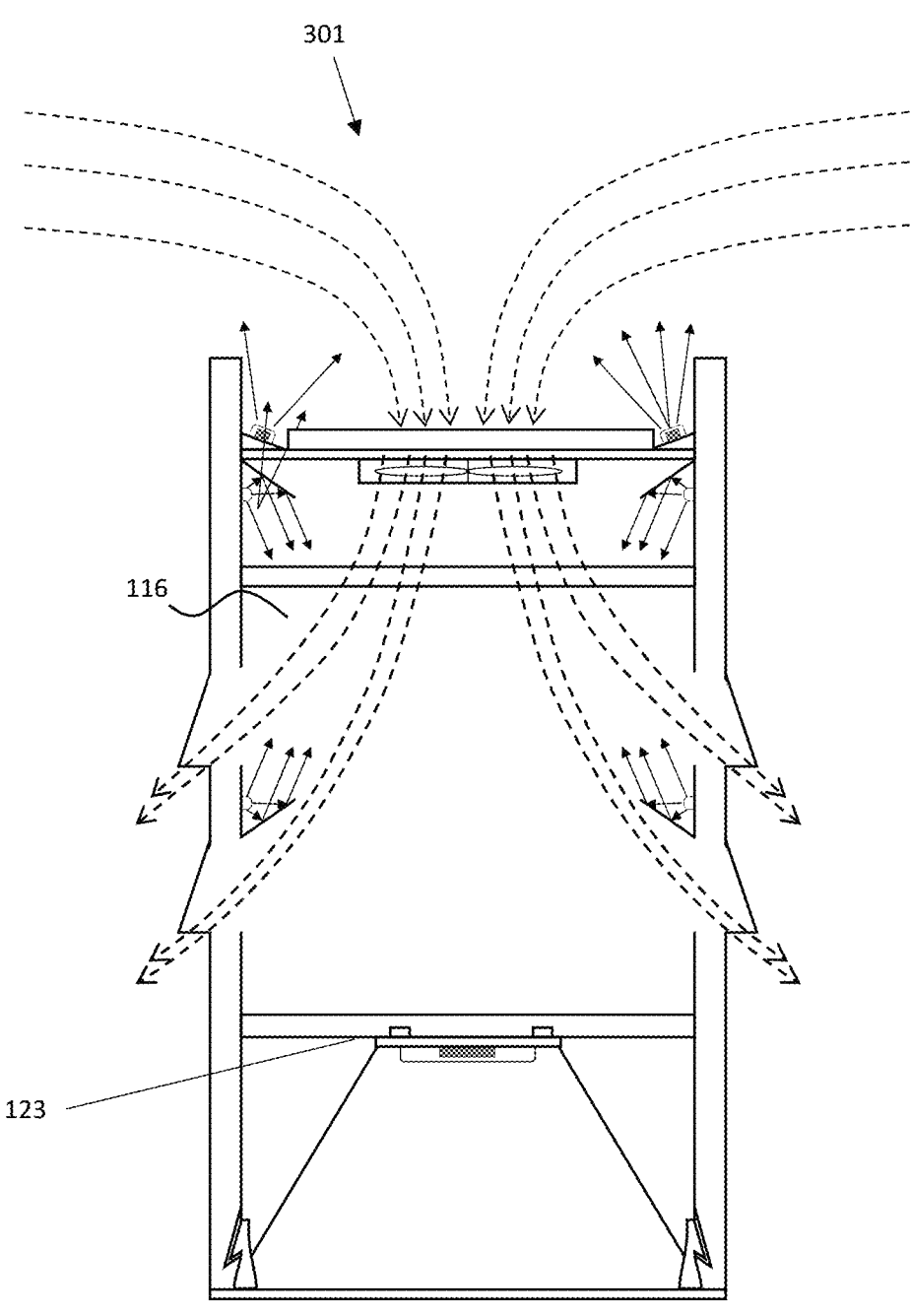
FIG. 3 shows an example light fixture with ultraviolet radiation sources, a fan and an air filter(s), consistent with disclosed embodiments.

Turning to figures, FIGS. 1-3 show various embodiments of light fixtures with ultraviolet radiation sources, a fan and air filters, consistent with disclosed embodiments. In an example embodiment, as shown in FIG. 1, light fixture 101 may include UV LED board elements 111 configured to irradiate air located above light fixture 101 (e.g., a region of air 109). In some cases, elements 111 may include optical elements (e.g., lenses, reflectors, and the like) for effectively directing UV radiation into region 109. In an example embodiment, elements 111 may be directed to region 109 to result in a target sterilization of air in region 109 (e.g., a log sterilization of a target virus in region 109). Additionally, fixture 101 may include one or more forced convection devices, such as, e.g., fans 112 configured to direct air from region 109 through an air filtering element 115. In an example embodiment, element 115 may be a pleated or non-pleated porous poly-tetra-fluoro-ethylene (PTFE) filter.

In an example embodiment, fans 112 may be secured in place using a perforated plate 113 configured to transmit air. In addition to elements 111, fixture 101 may also include additional UV LED sources 117 positioned and oriented to further sterilize air within an enclosure 116. In an example embodiment, sources 117 may include reflectors, or any other suitable optical elements for irradiating air within enclosure 116. In an example embodiment, internal surfaces of enclosure 116 may be reflective to ultraviolet radiation. For example, a lower surface of enclosure 116 may be a UV reflective cover 131. In some cases, sources 117 may be directed to irradiate a low surface 118 of filter 115. As shown in FIG. 1, air may be configured to exit through louver vents 119, and be directed substantially downwards, away from light fixture 101. In some cases, vents 119 may have adjustable openings, such as an opening 150 (e.g., a shape, an orientation, or a size of openings configured for transmitting air out of enclosure 116 may be adjustable).

In some cases, openings 150 and vents 119 can be configured to eliminate propagation of UV radiation to outside of light fixture 101. As shown in FIG. 1, light fixture 101 may further include a white LED source (or other sources of a visible radiation), such as a white LED board 132. In an example embodiment, source 132 may include optical elements such as lenses (e.g., a total internal reflection lens), mirrors, and the like. Further, source 132 may be connected to a heatsink 123 configured to transfer at least some of the heat generated by source 132 into ambient environment. As shown in FIG. 1, light fixture 101 may include a reflector 125 for directing some of the visible light generated by source 132 towards a diffuser 127. In an example embodiment, the diffuser may be made from any suitable material that is at least partially transparent to visible radiation. The diffuser may be configured to diffuse the visible radiation of source 132. The diffuser may be configured to connect to walls 140A and 140B via connection hooks 141A and 141B or the like.

In various embodiments, light fixture 101 may include driver electronics module 121 that may be placed at any suitable location within light fixture 101. In an example embodiment, module 121 may be configured to control any of operation of fans 112, UV LED sources 111 and 117, as well as source 132. In some cases, module 121 may be configured to adjust opening 150. In various embodiments, module 121 may be controlled wirelessly or through wired connection via an interface of a suitable electronic device. In an example embodiment, the suitable electronic device may be a smart phone, a computer, a tablet, a touch screen, an audio processing device (e.g., ALEXA®), or any other suitable device.

FIG. 2 shows an embodiment of light fixture 201 that may be a variation of the embodiment shown in FIG. 1. Light fixture 201 may include a dust pre-filter 211, as well as multiple sets of UV LED sources 213 configured to irradiate enclosures 216, as well as sides 218 of filter 215. FIG. 3 shows and example embodiment of fixture 301 (which may be similar to 101), in which driver electronics module 121 is not present, at least in vicinity of source 132 but installed remotely and connected via wired connection. Further, consistent with the embodiment shown in FIG. 3, a bottom part of enclosure 116 incudes a top portion of heat sink 123, allowing air within enclosure 116 to convectively cool heat sink 123.

Figure 4:
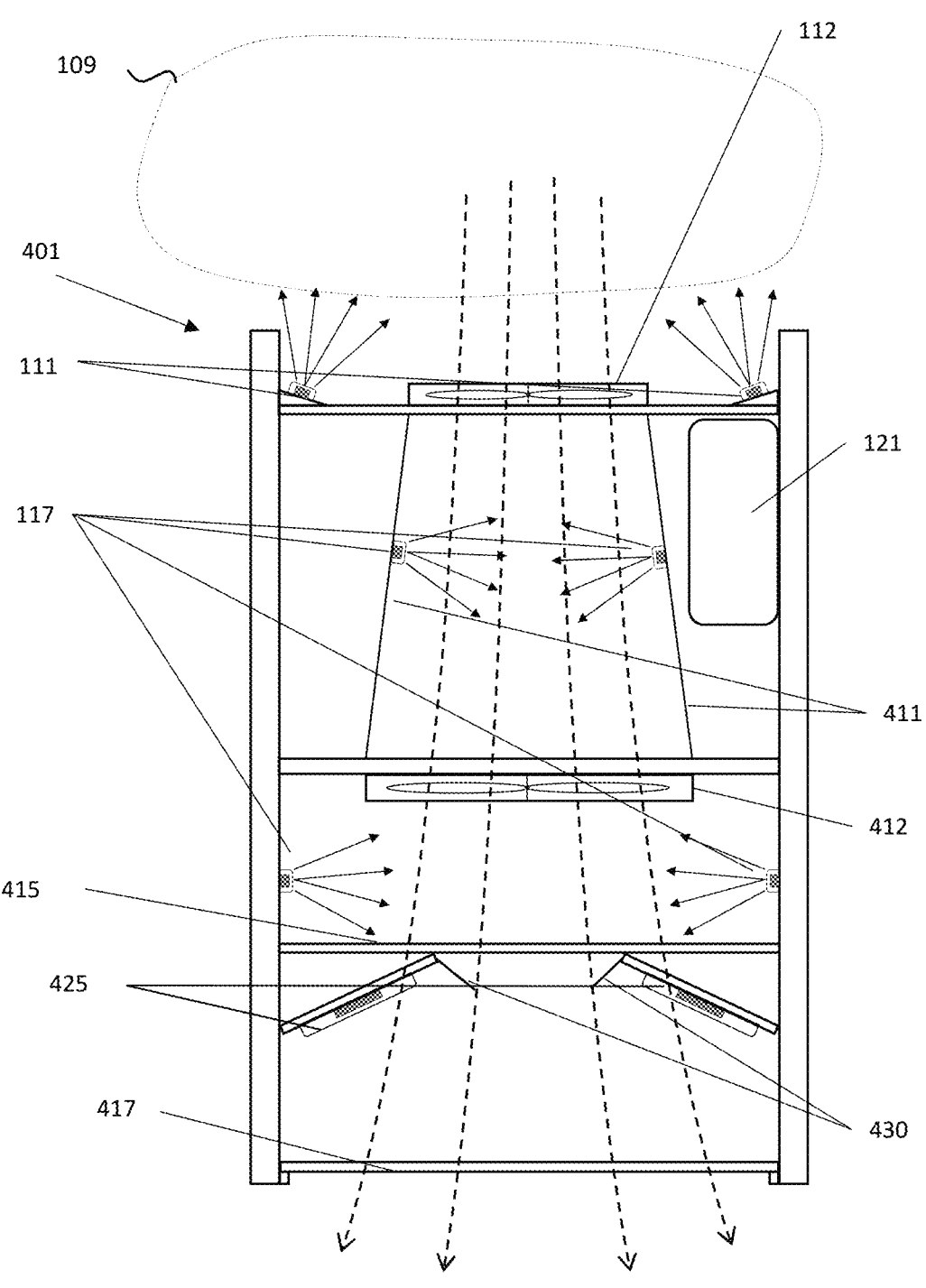
FIG. 4 shows an example embodiment of a light fixture with an air filter located at the bottom portion of a light fixture, consistent with disclosed embodiments.

FIG. 4 shows an example embodiment of a light fixture 401 including fan 112 configured to direct air from region 109 into an air duct 411. Additionally, or alternatively, a second air fan 412 may be also present and configured to move air within duct 411. In an example embodiment, multiple external UV LED sources 111 may be present, as described above. Further, internal UV LED sources 117 may be placed at different locations within light fixture 401. For instance, some of sources 117 may be placed within air duct 411, and some sources 117 may be placed underneath fan 412. Air duct 411 may include walls that are reflective to ultraviolet radiation (e.g., walls having an aluminum coating, a suitable polymer coating such as a PTFE, and the like). In an example embodiment, some of sources 117 may be configured to irradiate a surface of an air filter 415, as shown in FIG. 4.

In an example embodiment, visible light sources 425 may be positioned underneath filter element 415 and may be configured to emit light downwards from fixture 401 via an element 417. Light sources 425 may be protected from UV radiation using UV protective reflectors 430.

In an example embodiment, element 417 may be at least partially transparent to visible radiation. For instance, element 417 may be a visible light diffusing element. Additionally, in some cases, element 417 may also be transmittable to air. In an example embodiment, element 417 may be formed from a material that may be both transmittable to air and at least partially transparent to visible radiation and essentially not transparent to UV radiation. In some cases, element 417 may be an air filtering element. For instance, element 417 may be formed from a pleated or non-pleated porous poly-tetra-fluoro-ethylene (PTFE) filter. Additionally, or alternatively, element 417 may include holes for air transmission. In some cases, air may be configured to be transmitted around (e.g., around edges) of element 417.

As can be seen in the Figs. and, in particular, FIGS. 1-3, the filter 113 and filter assemblies in accordance with the present embodiments are exposed to UV radiation duration operation of the fixtures. The filters can be exposed to UV sources above, below and in between filters and filter layers. The incident UV radiation on the filters reduces the need to clean or replace the filters over time. The filters are preferably fabricated to be UV resistant and in some embodiments are bio-resistant to bacteria, viruses, mold etc. In particularly useful embodiments, the filters can include a pleated or non-pleated porous poly-tetra-fluoro-ethylene (PTFE) filter. In one embodiment, the filter, its housing, adhesives and other components are made to be UV resistant. The filter material itself, e.g., fibrous network materials, can include a porous PTFE material. The filter may have a pleated construction to reduce pressure drop across the filter due to larger material surface area incorporated into a size of the filter. Pleating is preferably sized to permit UV wavelength radiation to destroy bioparticles over the surface of the filter. The other filters components are preferably formed from a material having similar characteristics to that prevent biomaterials from growing and provide capture efficiency of above 99% and more preferably above 99.9%. In a particularly useful embodiment, one or more filters can include a porous network that can catch and collect biomatter and material that is stable under UV irradiation such that the organic contaminant can decompose on the surface of the filter under very high cumulating UV dose capable of breaking of, for example, carbon-carbon bonds and other chemical bonds in the organic biomaterial molecules.

In some cases, one or more air filters may be used with sets of UV LED sources (e.g., 115) may be installed at any suitable location within a cavity to further sterilize air and filters within the cavity. Sources may be directed towards filter surfaces to disinfect the filters at an inlet (or outlet) of the fixture. Bio-particles are trapped by the filter and have a higher density at the inlet. The present embodiments, permit the filter to be exposed to the UV radiation and concurrently clean the filter and the surrounding air. For example, some of the sources may be directed to disinfect the dust prefilter, and other sources may be directed to disinfect or decontaminate a pleated porous PTFE filter. In an example embodiment, the porous PTFE filter may be constructed to have the most penetrating particle size (MPPS) of less than 10 microns and, more preferably, less than 0.3 micron, and, more specifically, less than 0.1 microns.

By employing, e.g., porous PTFE bound to a substrate, tensile strength and elongation at break point is increased; therefore, the useful filter life under UV irradiation is also increased. In one example, the PTFE material can not only filter less than 0.1 micron particles for greater than 99.0% efficiency but can sustain an extended or indefinite life even at high irradiation rates, e.g., hundreds of mJ/cm² under normal particle loads.

The PTFE material is stable and maintains a collection efficiency under very harsh UV exposure conditions. In useful embodiments, high UV dosages of at least 1000's of mJ/cm² to 10000's of mJ/cm² can be achieved with longer life where a dose to inactivate, e.g., the COVID-19 virus on a surface varies from 15 to 40 mJ/cm². The UV exposed filter in accordance with the present embodiments facilitates surface disinfection in addition to direct air disinfection and can filter material while recycling UV radiation inside a cavity, since PTFE material is highly reflective in the UV spectral range. In one embodiment, the filter material can be pleated for lower pressure drop across the filter. In addition, by dispersing UV sources between filter layers, particles can be dispersed and the filters treated with UV to reduce pressure drop and ensure the destruction of pathogens. In other embodiments, other UV compatible materials and coatings may also be employed.

Figure 5A:
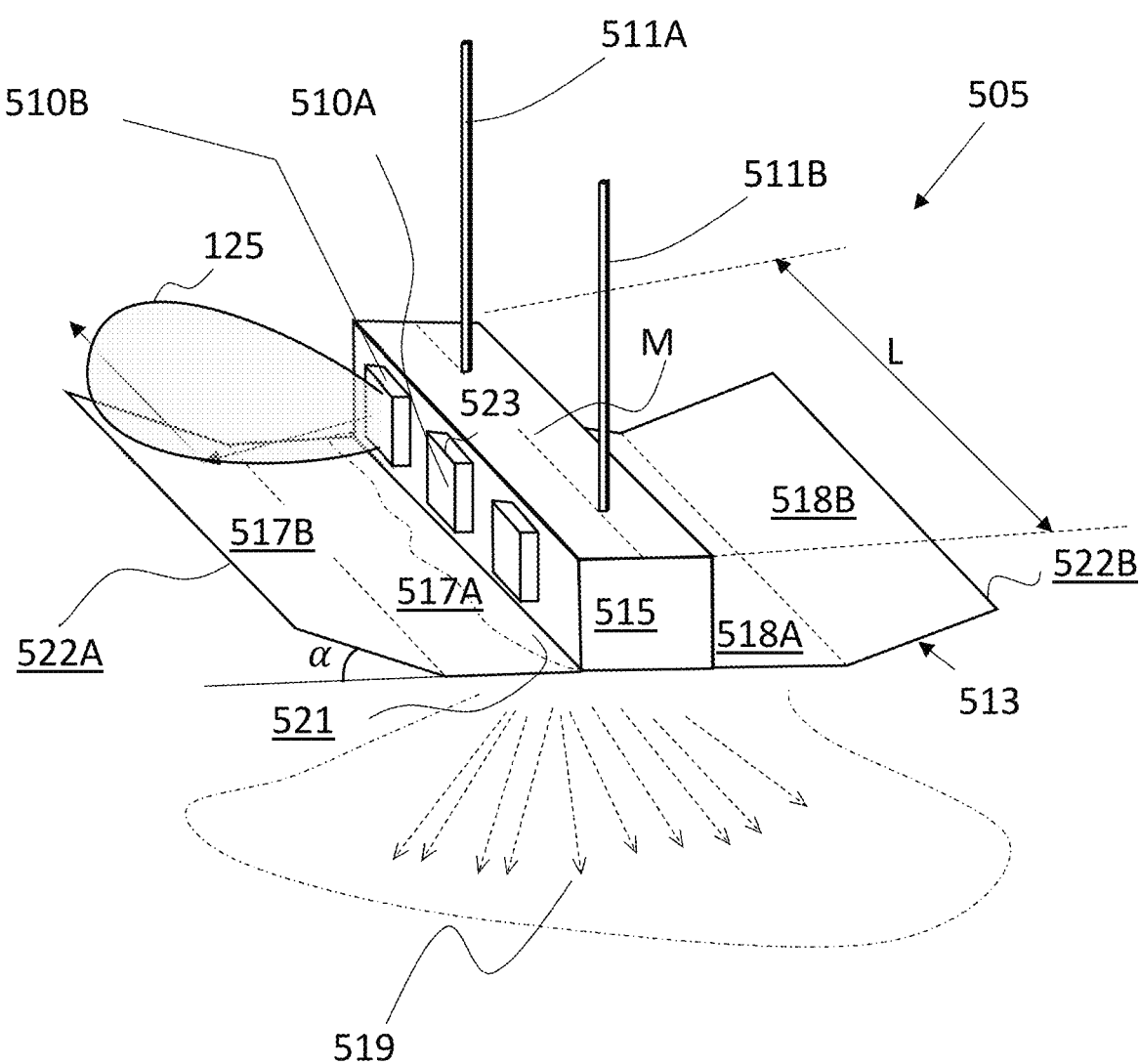
FIG. 5A illustrates an example embodiment of a light fixture, including ultraviolet radiation sources for irradiation of upper room space, consistent with disclosed embodiments.
Figure 5B:
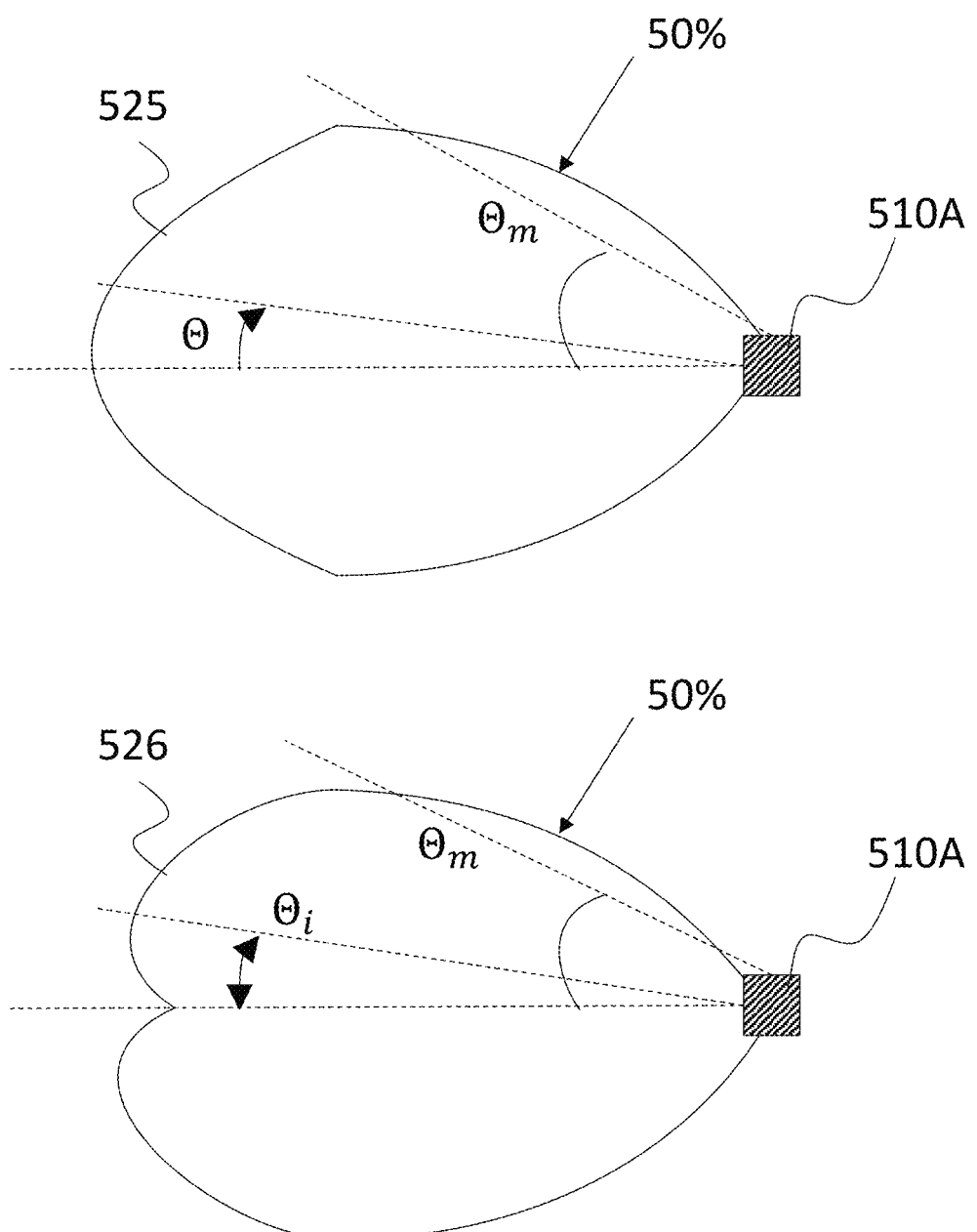
FIG. 5B illustrates an example distribution of ultraviolet radiation intensity for an ultraviolet light emitting diode, consistent with disclosed embodiments.

FIG. 5A illustrates another example embodiment of a light fixture 505 of length L, including ultraviolet radiation sources 510A, 510B, and the like, for irradiation of upper room space, consistent with disclosed embodiments. In an example embodiment, ultraviolet radiation sources 510A and 510B may be ultraviolet light emitting diodes (UV LEDs) with a wavelength ranging, e.g., between 230 to 360 nanometers. In an example embodiment, the intensity of UV LED sources may range between, e.g., 1 mW and 10 W. An example single UV LED source may be a printed circuit board (PCB) with one or more UV LEDs, as well as suitable optical elements (e.g., lenses, prisms, mirrors, reflective scattering elements, and the like) and/or a protective window. An example distribution of intensity 525 of an illustrative UV LED source (e.g., UV LED 510A) is shown in FIG. 5B, with the highest intensity illuminated at angle θ=V. In an example embodiment, most of the radiation may be within a half-angle $\Phi_m$, as shown in FIG. 5B.

For example, at angle $\Phi_m$ ultraviolet radiation may be, e.g., fifty percent, forty percent, thirty percent, twenty percent, fifteen percent, ten percent, five percent, one percent, and the like, of ultraviolet radiation at a peak value (i.e., at the angle θ). In an example embodiment, angle $\Phi_m$ can be 5 degrees, 10 degrees, 15 degrees, 20 degrees, 25 degrees, 30 degrees, or few tens of the degrees, etc. FIG. 5B also shows another angular distribution of intensity 526, for which the maximum value of ultraviolet intensity may be achieved at an angle θ=$\theta_i$ that is larger than zero degrees (e.g., $\theta_i$ may be between a few degrees to a few tens of the degrees).

Returning to FIG. 5A, light fixture 505 may have several UV LEDs positioned on the left side and the right side of a lighting fixture housing 515. For example, as shown in FIG. 5A, UV LED sources 510A and 510B are located on the left side. In an example embodiment, a light fixture may have a characteristic length L, as shown in FIG. 5A, and may be suspended from a ceiling using suspension members 511A, 511B, and the like. In an example embodiment, suspension members may be solid elements (e.g., rods) or flexible elements (e.g., wires or cables). In an example embodiment, members 511A, 511B may be used not only to suspend a light fixture 505 but also for conducting electrical power to fixture 505 and/or for communicating data represented by digital electrical signals to and from fixture 505. In an example embodiment, fixture 505 may include a reflector 513, which may include several surfaces such as surfaces 517A and 517B, shown on the left side of reflector 513. Reflector 513 may have similar surfaces 518A and 518B on the right side of reflector 513. In an example embodiment, reflector 513 may be symmetric about a midline M, as shown in FIG. 5A.

In an example embodiment, surface 517B and 518B may form an angle α with horizontal and be bent relative to corresponding surfaces 517A and 517B, as shown in FIG. 5A. The angle α may be in a range of, e.g., 0 to 60 degrees, but in some example embodiments, the angle α may be between 5 and 25 degrees. In various embodiments, the intensity of ultraviolet radiational sources (e.g., UV LEDs 510A and 510B) may be selected to result in air sterilization. In an example embodiment, the air sterilization may be achieved if a parcel of air receives a target radiational dose (e.g., between 0.01 W/m$^2$ and 10 W/m$^2$).

In various embodiments, reflector 513 may be configured to reflect ultraviolet radiation emitted by UV LEDs towards an upper portion of a room in which light fixture 505 is located. For example, reflector 513 may be designed to ensure that no amount of ultraviolet radiation is reflected downwards towards a lower portion of the room where people may be located. In an example embodiment, reflector 513 may not be transparent (e.g., opaque to UV wavelengths) to the ultraviolet radiation. Reflector 513 may have a top surface, the top surface comprising a distant region (e.g., region 517B) and an adjacent region (e.g., region 517A), wherein at least a portion of the adjacent region (e.g., a region 521, as shown in FIG. 5A) is located close to and below the ultraviolet radiation sources (e.g., UV LEDs 510A and 510B), and wherein the distant region comprises a rim (e.g., the rim may be made from edges 522A and 522B) located above a top-most emitting point (e.g., the top-most emitting points may be located up to region 523, as shown in FIG. 5A) of the ultraviolet radiation source (e.g., source 510A). In various embodiments, reflector 513 may have at least a partially reflective surface with reflectivity of preferably at least 80% in the ultraviolet region (i.e., at a wavelength in a range of 230-360 nm), although lower reflectivities are contemplated. As shown in FIG. 5A, light fixture 505 may have a visible light emitting source 519 adjacent to the bottom part of reflector 513. Source 519 may be configured to emit visible light towards a bottom portion of the room for illuminating objects in the bottom portion of the room. In various embodiments, the room may be configured so that ultraviolet light radiation does not reflect significantly from the ceiling and walls of the room towards the bottom portion of the room.

Figure 5C:
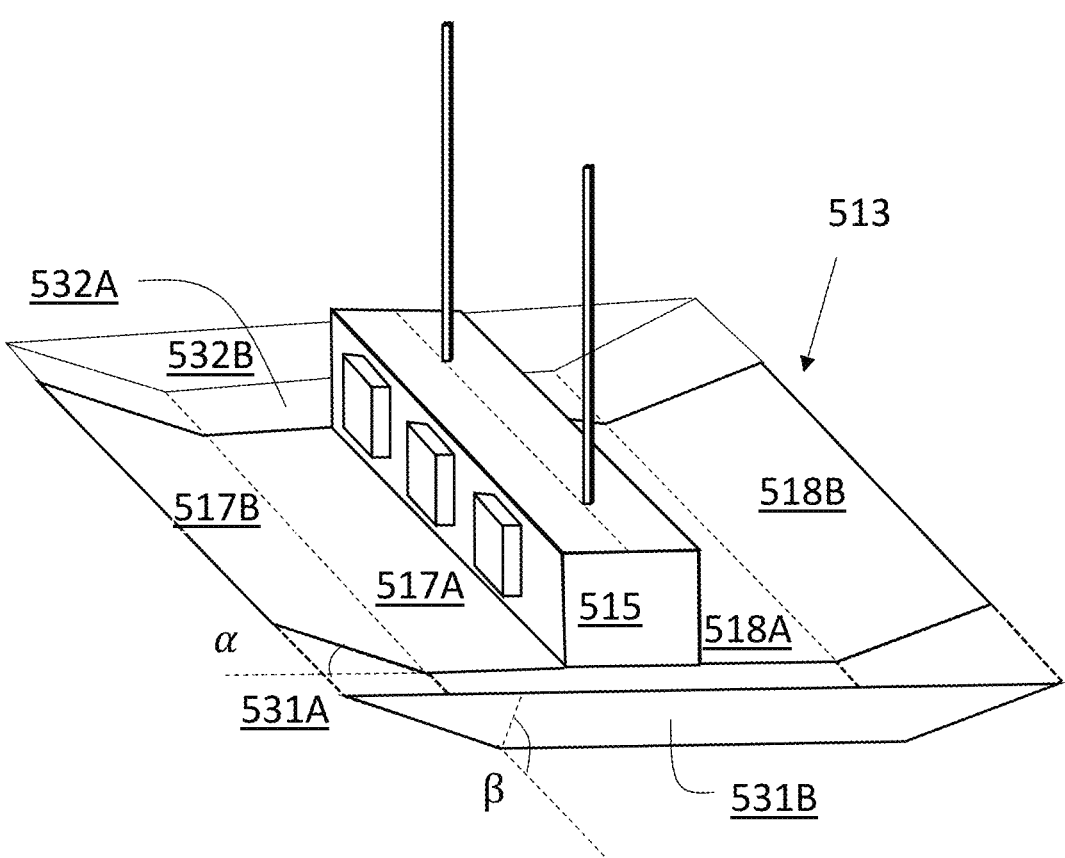
FIG. 5C illustrates example surfaces of a reflector of a light fixture, consistent with disclosed embodiments.

It should be noted that light fixture 505 may have any suitable control system for controlling the intensity of ultraviolet light emitting sources. In some cases, the control system may be configured to control the distribution of ultraviolet light emitting radiation by moving either UV LEDs, moving surfaces of reflector 513 (e.g., in some cases, angle α may be adjusted), or moving optical elements that may be adjacent to (or part of) ultraviolet light emitting sources. While it is shown that reflector 513 may have several surfaces (e.g., 517A and 517B in a rectangular configuration), reflector 513 may have any number of surfaces and may have any suitable shape for reflecting ultraviolet radiation from UV LED source towards an upper portion of the room, e.g., hexagonal-shaped, round, square, etc. In some cases, reflector 513 may have front surfaces 531A and 531B, and back surface 532A and 532B, as shown in FIG. 5C, with at least some of the front surfaces (e.g., surface 531B and 532B) bending upwards at a prescribed angle (e.g., angle β).

Figure 6A:
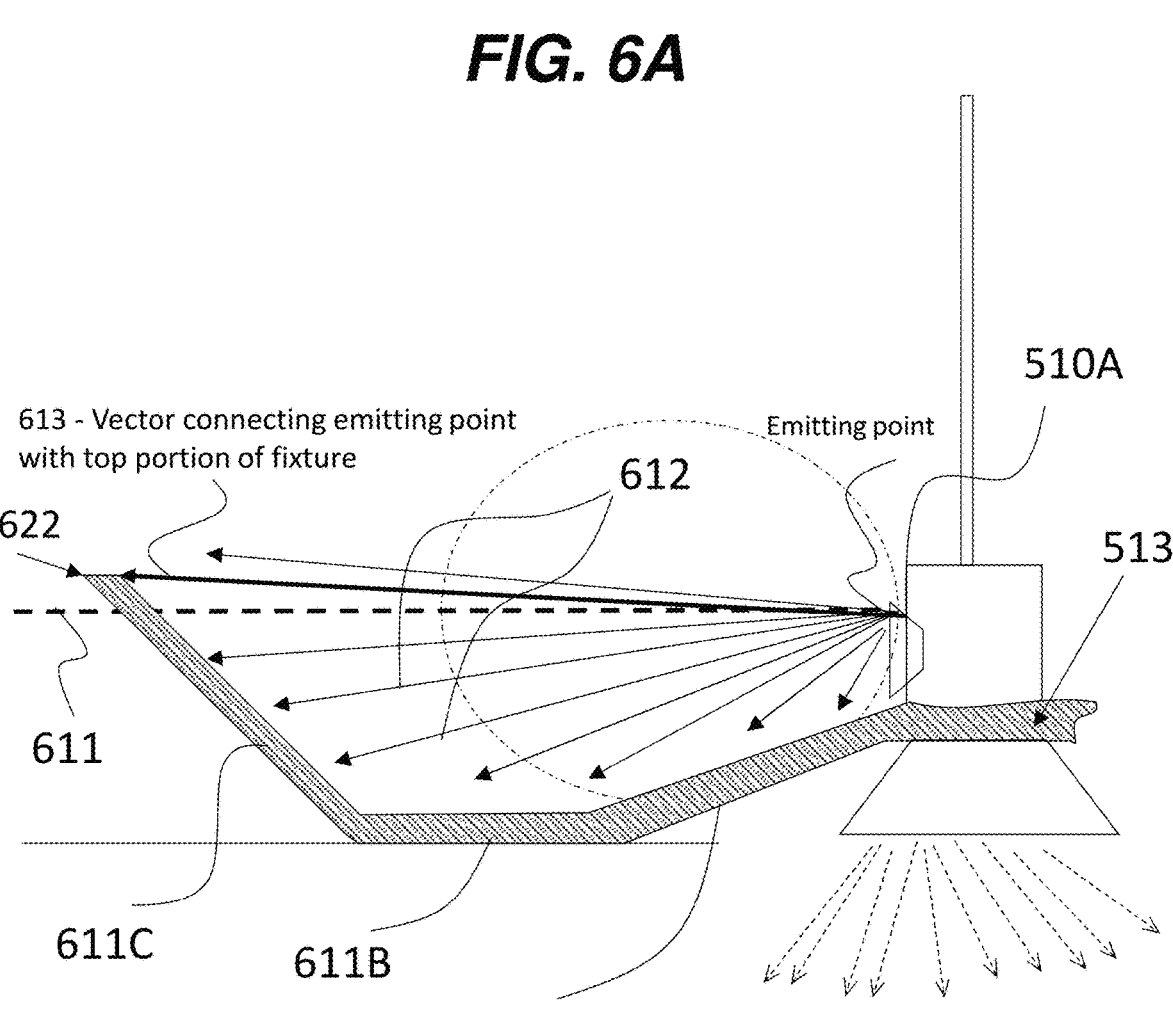
FIG. 6A illustrates an example reflector for the light fixture, consistent with disclosed embodiments.
Figure 6A:
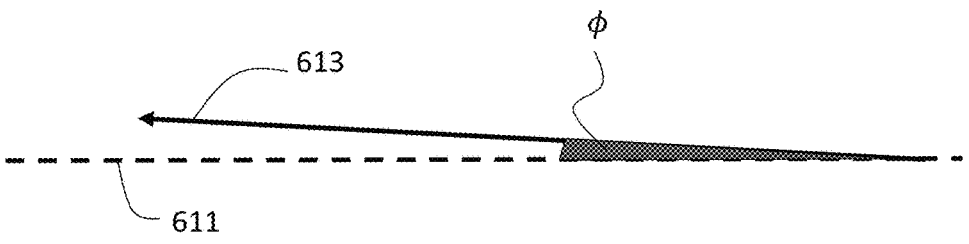
Figure 6B:
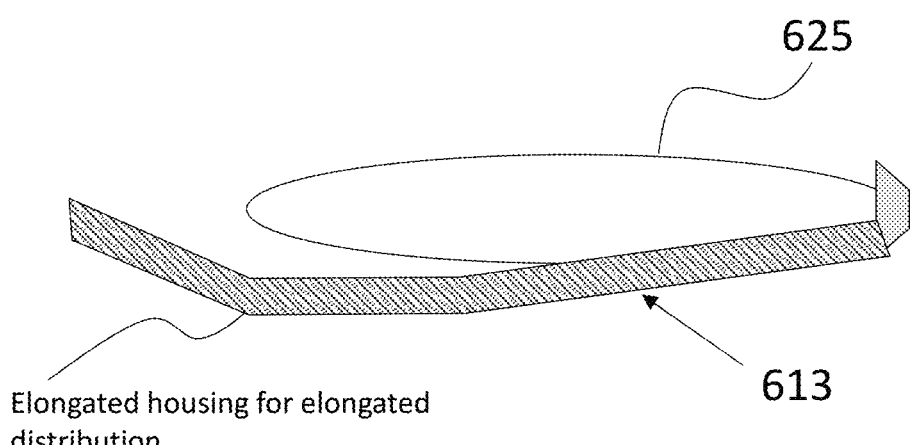
FIG. 6B illustrates an example reflector for the light fixture, consistent with disclosed embodiments.
Figure 6C:
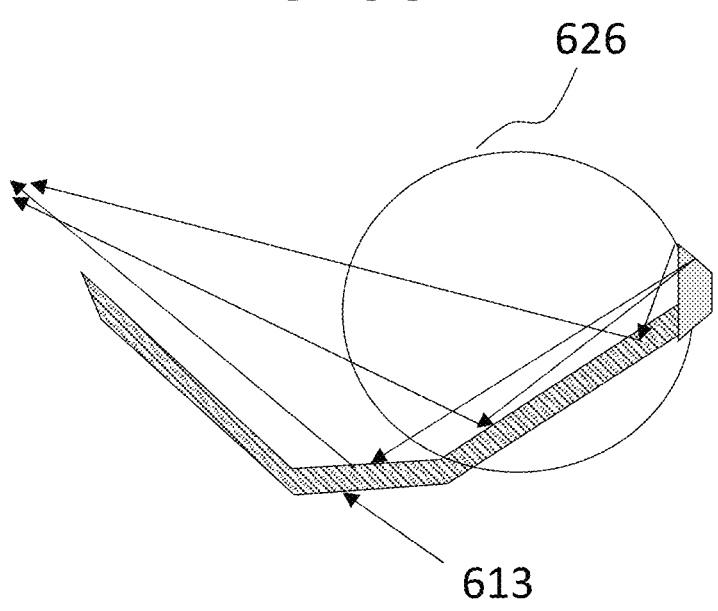
FIG. 6C illustrates an example reflector for the light fixture, consistent with disclosed embodiments.

FIGS. 6A-6C illustrate examples of reflector 513 for the light fixture, consistent with disclosed embodiments. For example, FIG. 6A shows a reflector 513 having sections 611A-611C from which rays 612 may be reflected towards a region (also referred to as a volume) of air above reflector 513. In various embodiments, to ensure that ultraviolet radiation from an example source 510A is not emitted at any region below reflector 513, reflector 513 may include a rim 622 that may be above any other point of reflector 513 and may also be above the highest emitting point of source 510A. For example, a vector 613 drawing from at least one highest emitting point of source 510A may have a non-zero angle φ with a horizontal line 611, as shown in FIG. 6A. FIGS. 6B and 6C show different embodiments of reflector 513 for different distributions of intensities 525 and 526. In various embodiments, reflector shape 513 may be chosen (i.e., tailored) for particular intensity 525 or 526 emitted by source 510A. The reflector shape 513 is not limited to the examples shown.

Figures 7A, 7B:
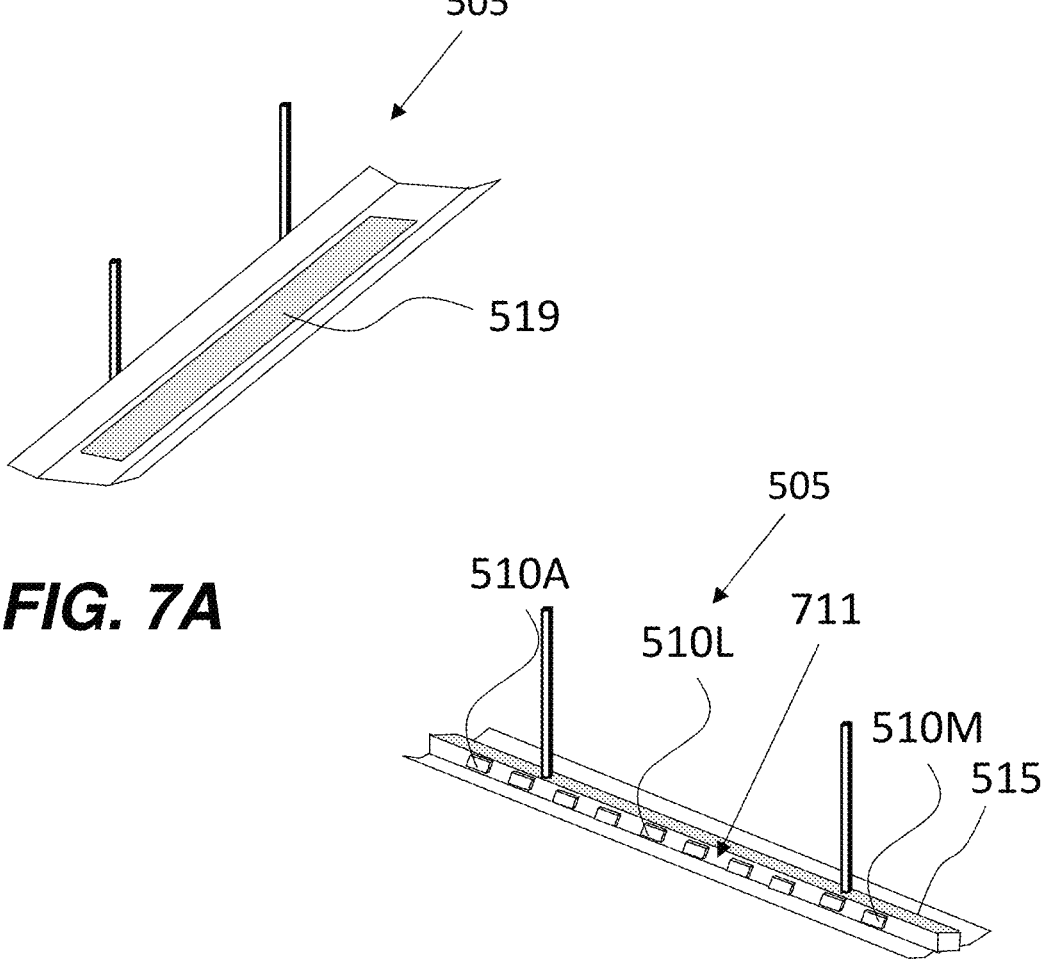
FIG. 7A illustrates an example view of a light fixture with ultraviolet radiation sources, consistent with disclosed embodiments.
FIG. 7B illustrates an example view of a light fixture with ultraviolet radiation sources, consistent with disclosed embodiments.

FIGS. 7A-7B illustrate example views of a light fixture with ultraviolet radiation sources, consistent with disclosed embodiments. In an example embodiment, FIG. 7A shows light fixture 505 as viewed from the bottom of fixture 505, while FIG. 7B shows fixture 505 as viewed from the side of fixture 505. Fixture 505 includes a source of visible light 519, as indicated in FIG. 7A. As shown in FIG. 7B, multiple UV light sources may be installed on housing 515. As described above, such UV light sources may be PCB boards populated with UV LEDs and UV transparent optical element (e.g., lens or window). Single pass transmission of such optical elements should be preferably at least 70% or higher at the peak emission wavelength of the UV LEDs. In an example embodiment, housing 515 may have electrical wiring and a control system for electrically powering and controlling the operation of the UV LEDs. In some embodiments, a control system for controlling one or more light fixtures may be installed elsewhere (i.e., not within housing 515 of fixture 505). In some embodiments, UV LED 510A may be a UV LED source containing a plurality of UV LEDs. For example, UV LED 510A may be a printed circuit board containing multiple UV LEDs. In some cases, multiple boards 510A-510M may be installed on a side 711 of housing 515. For example, there can be a few boards or as much as a few tens of boards.

Figures 8A, 8B:
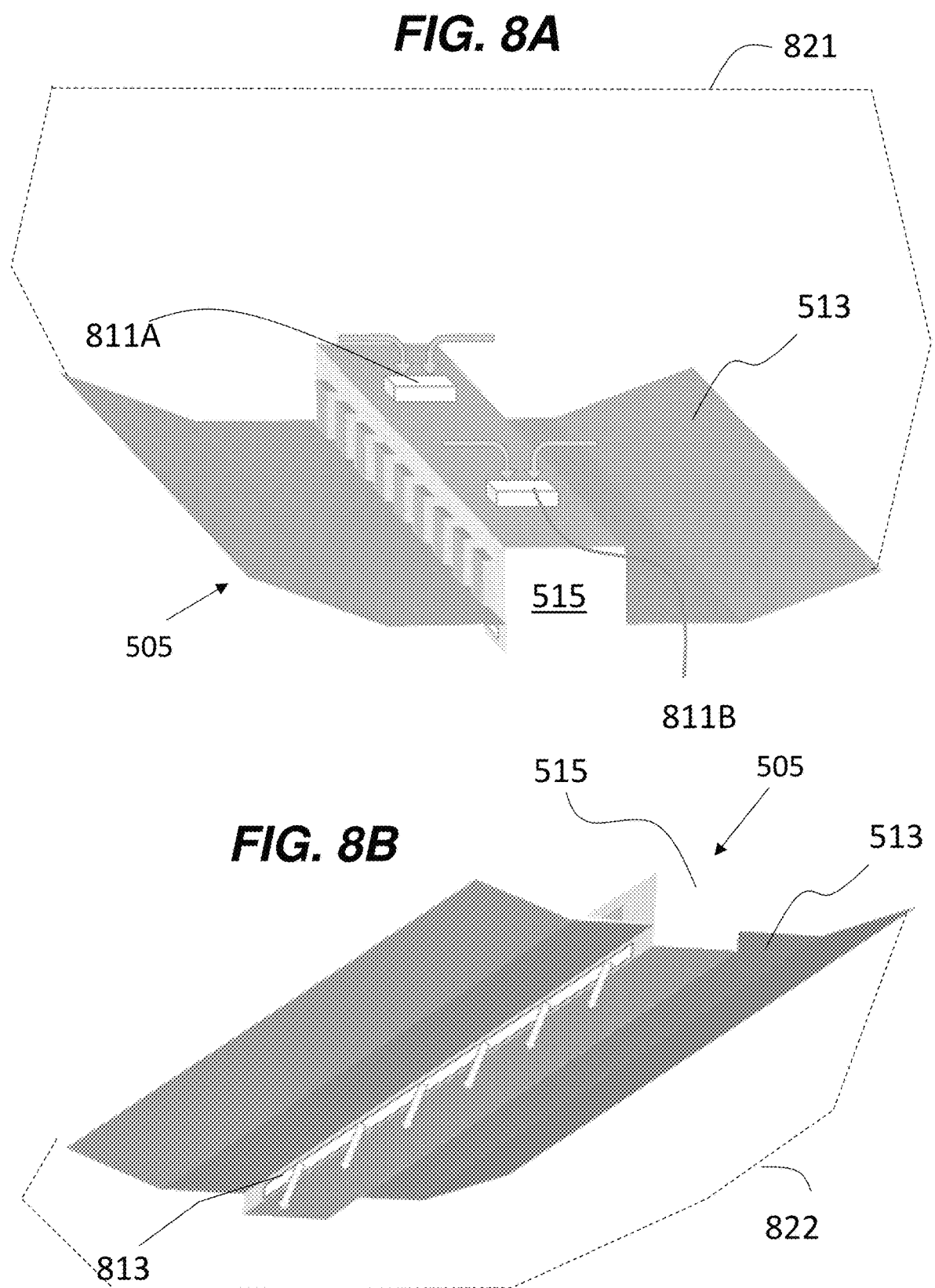
FIG. 8A illustrates an example light fixture with airflow controlling elements, consistent with disclosed embodiments.
FIG. 8B illustrates an example light fixture with airflow controlling elements, consistent with disclosed embodiments.

FIGS. 8A-8B illustrate example light fixtures with airflow controlling elements 811A, 811B, consistent with disclosed embodiments. FIG. 8A shows a 3-dimensional view of reflector 513 and housing 515 of light fixture 505. As shown in FIG. 8A, housing 515 may include air controlling elements 811A and 811B. These elements may be, for example, forced convection devices, e.g., fans, configured to flow air from a volume 821 located above light fixture 505 towards a bottom portion of a room (i.e., below light fixture 505, towards volume 822, as shown in FIG. 8B). In an example embodiment, flow controlling elements 811A and 811B may flow air from an opening 813 in housing 515, as shown in FIG. 8B.

Figure 8C:
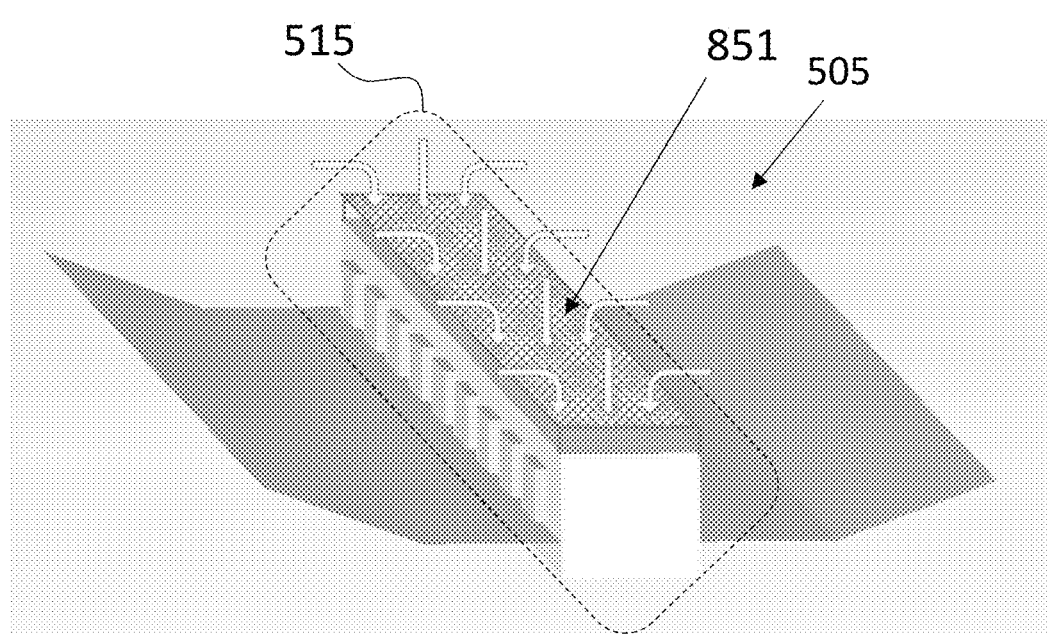
FIG. 8C illustrates an example light fixture with airflow controlling elements, consistent with disclosed embodiments.
Figure 8C:
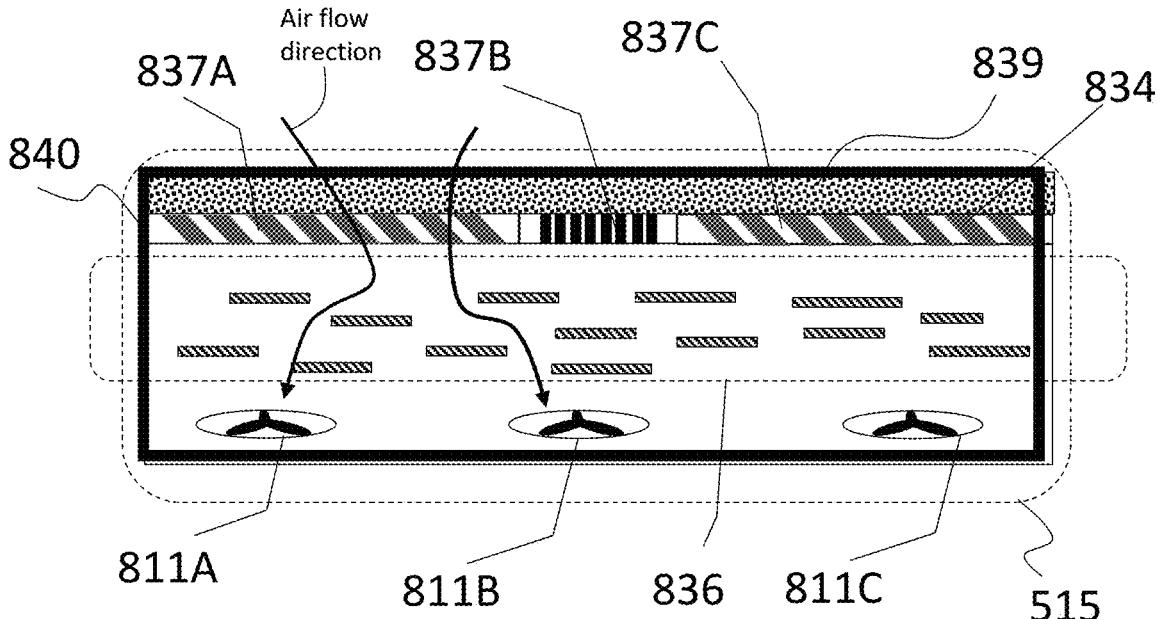

FIG. 8C shows an example light fixture 505 in cross-section with flow controlling elements 811A-811C. Light fixture housing 515 may include various flow control elements 839, 837A-837C, and 836 for controlling air flow through cavity 840 contained in housing 515. As shown in FIG. 8C, elements 811A-811C may include fans, and elements 836 may be surfaces for controlling the flow. For example, elements 836 may be positioned to help increase the uniformity of air flow through the top portion 851 of housing 515. In some cases, elements 839 and 837A-837C may include a set of meshes or porous slabs (e.g., element 839) for improving the uniformity of air flow through cavity 840. In some cases, a particular distribution of air flow through surface 851 may be required and may be configured by positioning elements 836 and selecting meshes 837A-837C. In some cases, meshes 837A-837C may have inclined pores 834, pores of variable size (e.g., sizes of pores may vary for different sections of surface 851), pores of variable density throughout surface 851, and the like. For example, meshes 837A-837C, element 839, and elements 836 may be configured to provide a higher air flow rate at the sides of surface 851 than at the center of surface 851. Alternatively, the middle section of surface 851 may have a higher flow rate at the center of surface 851. In various embodiments, elements 839, 837A-837C, and 836, are configured to provide a required air flow rate through cavity 840.

Figure 9:
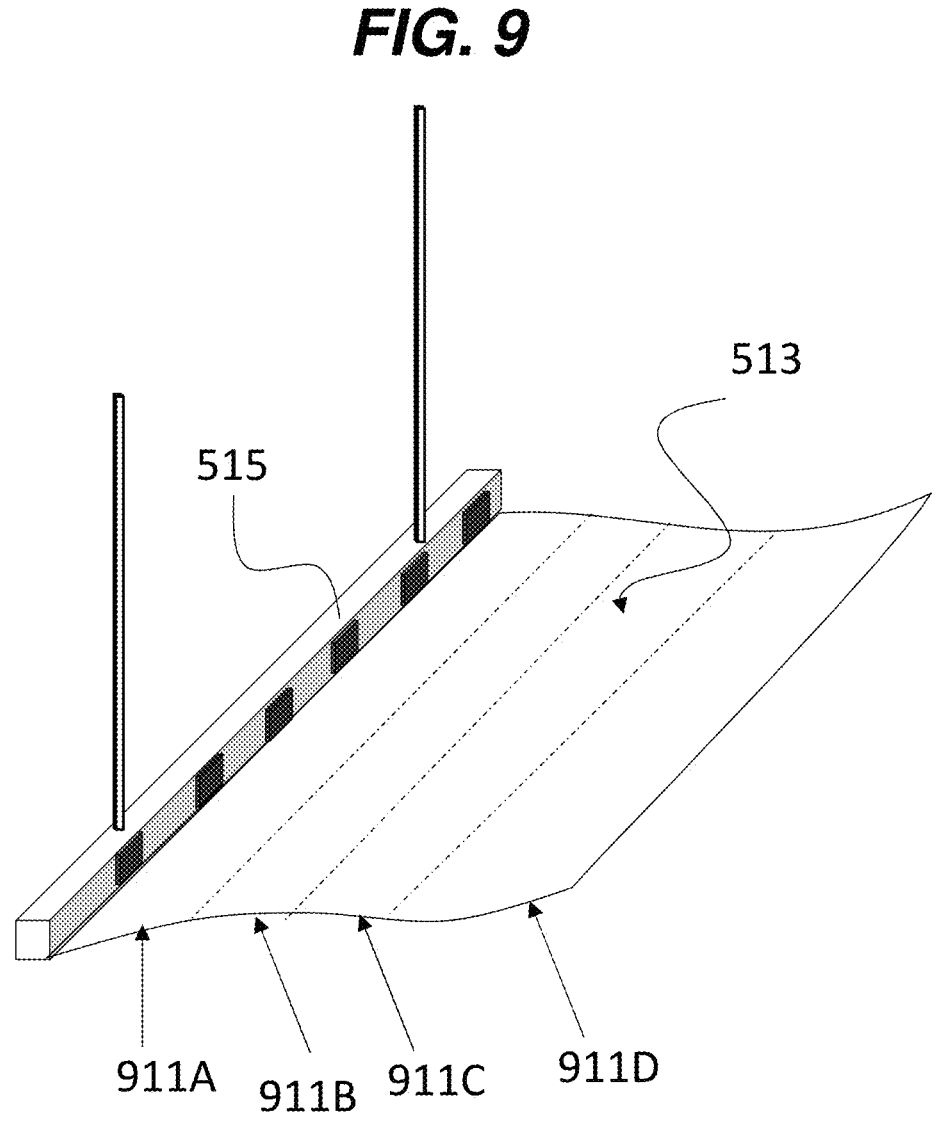
FIG. 9 illustrates an example reflector for a light fixture, consistent with disclosed embodiments.

FIG. 9 illustrates another example of reflector 513 for a light fixture, consistent with disclosed embodiments. The reflector may include multiple surfaces 911A-911D, with surfaces positioned and oriented to provide a target ultraviolet radiation intensity above light fixture 505. Only a left side of reflector 513 is shown attached to housing 515, and a right side of reflector 513 may be formed to have the same shape, such that reflector 513 is symmetric about housing 515. In other embodiments, the reflectors 513 may be asymmetric to provide a desired appearance or to fit in a selected location. Other reflector profiles are also contemplated.

Figure 10:
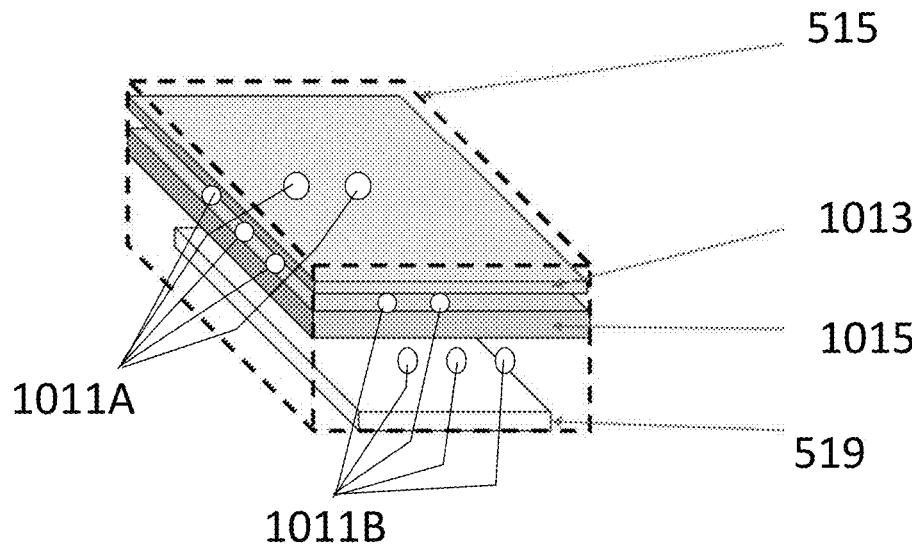
FIG. 10 is an example cavity located within a light fixture, with the cavity containing air filters, consistent with disclosed embodiments.

As previously shown in Figs. SA and 8B, air controlling elements may be installed into housing 515. In various embodiments, the air is obtained from a top portion of a room (e.g., from air volume 821, as shown in FIG. 8A) and is moved towards a bottom portion of the room (e.g., towards air volume 822, as shown in FIG. 8B). Light fixture 505 may be configured to irradiate volume 821 with ultraviolet light such that any parcel of air (i.e., any small portion of air found in volume 821) is thoroughly sterilized prior to moving from volume 821 to volume 822. Further, during airflow from volume 821 to volume 822, air may pass through a duct (herein, also referred to as a cavity) located in housing 515, as shown in FIG. 10. It should be noted that the UV radiation from sources that is reflected by the reflectors purifies the air entering any inlet filters and treats the filters as well for the described embodiments.

In an example embodiment, the duct may include one or more filters. In an example embodiment, the duct may have a first filter 1013 that may be a dust prefilter, a high-efficiency particulate arrestment (HEPA) filter, and the like, and a second filter 1015 that may be a pleated or non-pleated porous poly-tetra-fluoro-ethylene (PTFE) filter. In some cases, more air filters may be used. In some cases, another set of UV LED sources 1011A and 1011B may be installed at any suitable location within a cavity to further sterilize air within the cavity. In some cases, sources 1011A and 1011B may be directed towards filter surfaces to disinfect the filters. For example, at least some of the sources (e.g., sources 1011A) may be directed to disinfect the dust prefilter, and other sources (e.g., sources 1011B) may be directed to disinfect or decontaminate a pleated porous PTFE filter. In an example embodiment, the porous PTFE filter may be constructed to have the most penetrating particle size (MPPS) of less than 10 microns and, more preferably, less than 0.3 micron, and more specifically, less than 0.1 microns.

Figure 11:
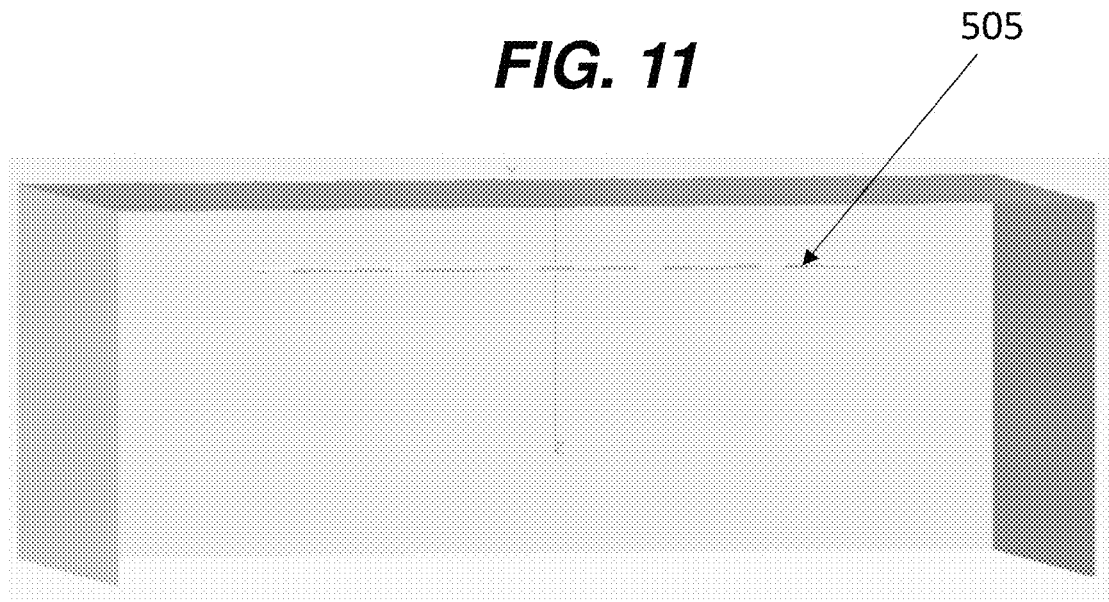
FIG. 11 is an example placement of a light fixture within a room, consistent with disclosed embodiments.
Figure 12:
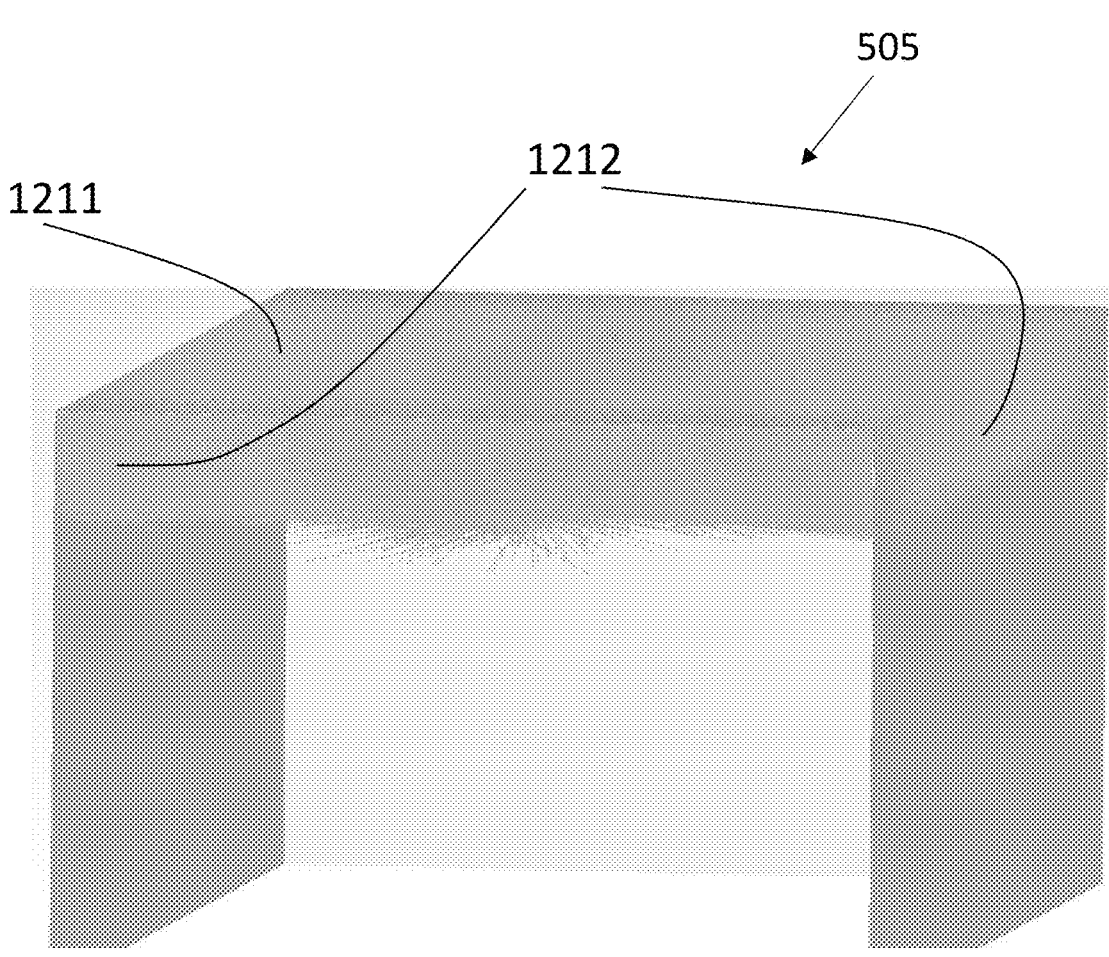
FIG. 12 is an illustrative distribution of ultraviolet light rays throughout an upper room space, consistent with disclosed embodiments.

FIGS. 11 and 12 show an example placement of a light fixture within a room and an illustrative distribution of ultraviolet light rays throughout an upper room space, consistent with disclosed embodiments. As shown in FIG. 11, fixture 505 may be elongated and extend through a large portion of a room. In an example embodiment, the room may be a conference room, and fixture 505 may extend over a significant length of the room (e.g., 40%, 50%, 60% of the room length, and the like. In an example embodiment, fixture 505 may be separated from a ceiling by a distance of a few inches to a few feet. In some cases, more than a few feet may separate fixture 505 from the ceiling. Light fixture 505 may extend in a middle portion of an elongated room and be positioned at about an equal distance from various walls of the room. For larger rooms, to thoroughly disinfect the air, multiple light fixtures 505 may be located within a room. In an example embodiment, light fixtures 505 may be distributed within a room to result in the distribution of ultraviolet radiation intensity such that all the air in the upper portion of the room is thoroughly disinfected. FIG. 12 shows a simulated distribution of rays from light fixture 505. At least some of the rays of ultraviolet radiation reach ceiling and contributes to an ultraviolet radiation distribution 1211 over the ceiling. Additionally, some of the ultraviolet radiation reaches side walls of the room and contributes to an ultraviolet radiation distribution 1212 over the walls of the room.

Figure 13:
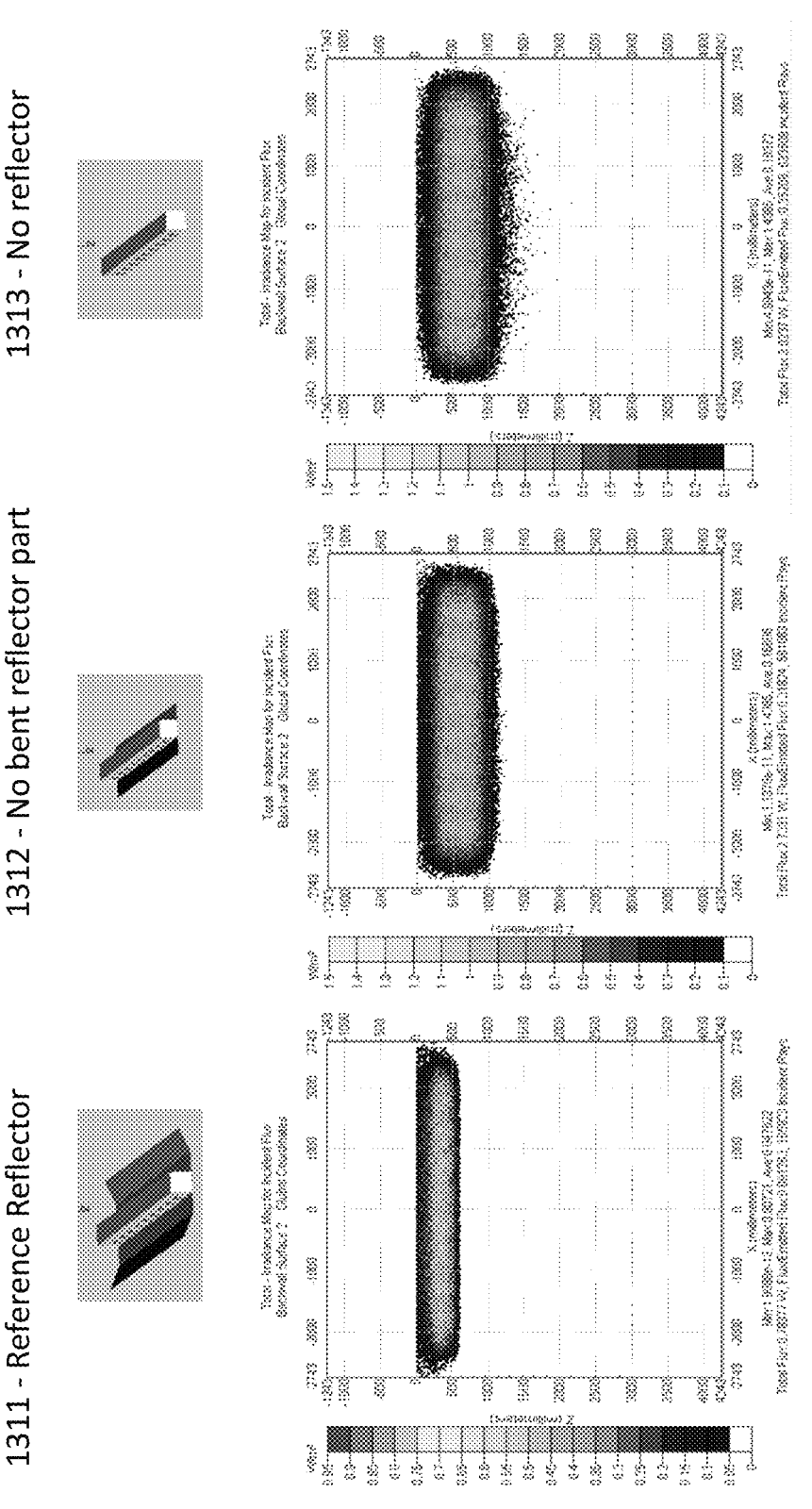
FIG. 13 is an example distribution of ultraviolet light intensity over a side wall of a room obtained for different reflectors, the ultraviolet light radiated from ultraviolet light sources of light fixture, consistent with disclosed embodiments.
Figure 14:
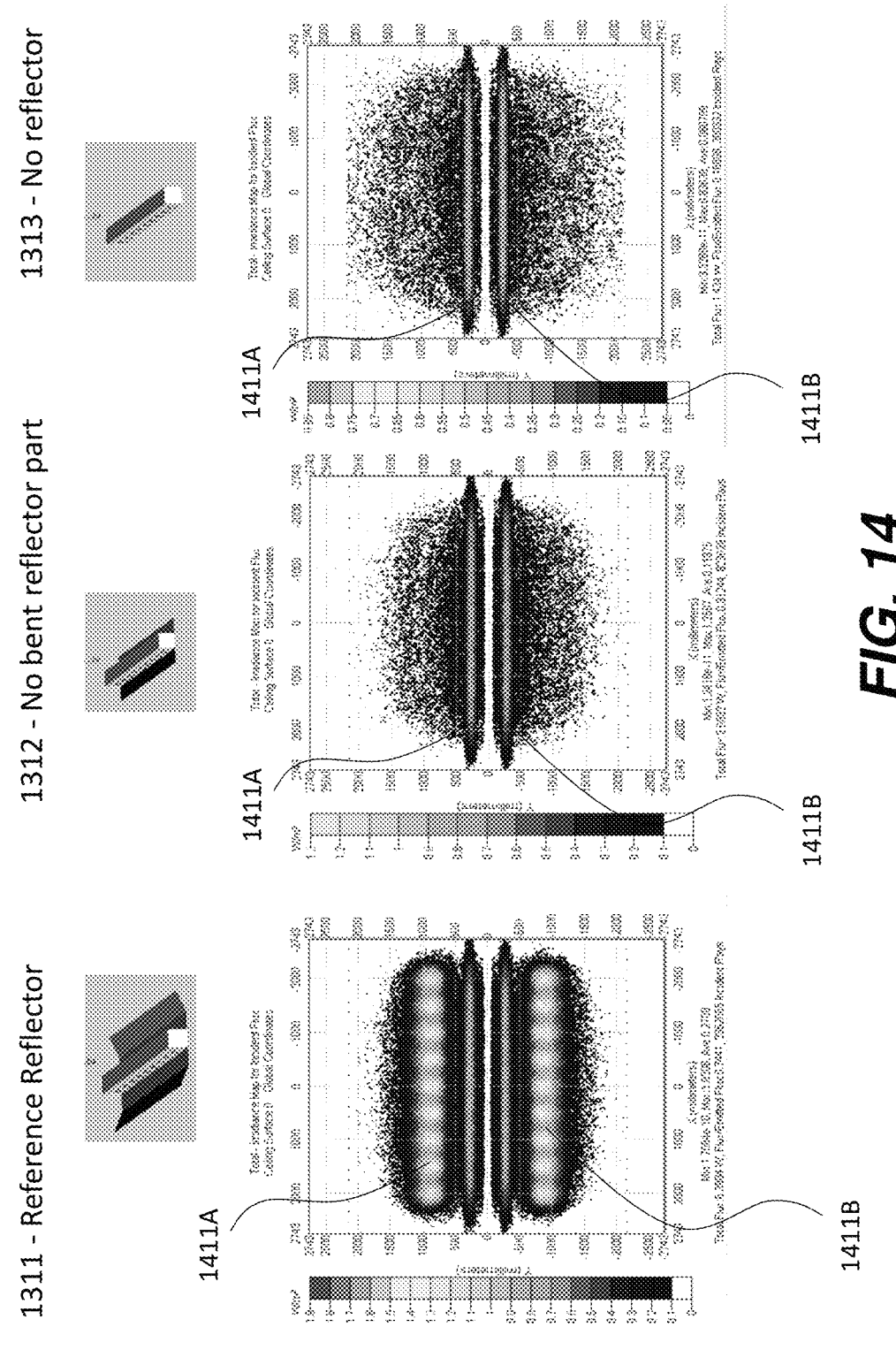
FIG. 14 is an example distribution of ultraviolet light intensity over a ceiling of a room obtained for different reflectors, the ultraviolet light radiated from ultraviolet light sources of light fixture, consistent with disclosed embodiments.
Figure 15:
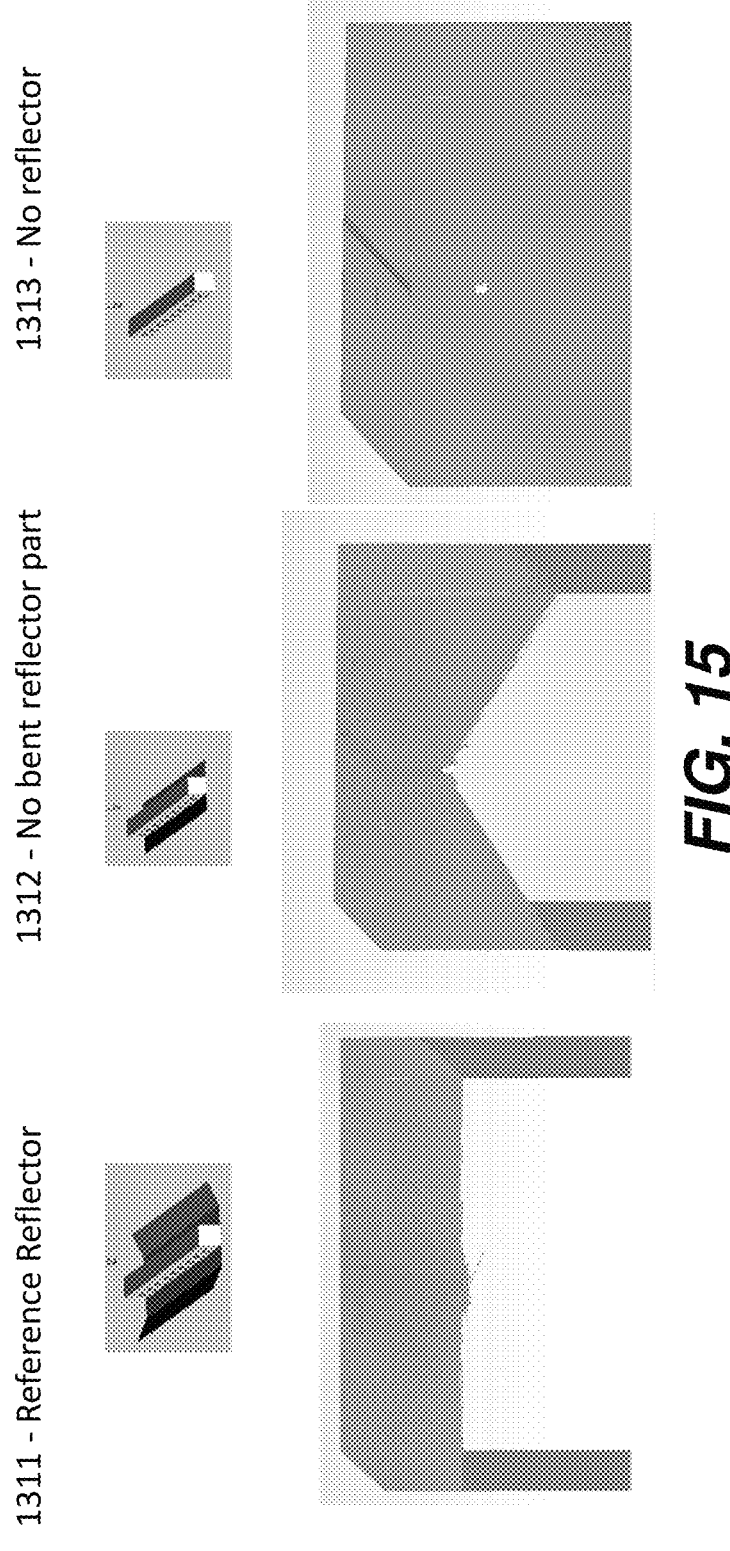
FIG. 15 is an illustrative distribution of ultraviolet light rays throughout an upper room space for different reflectors, consistent with disclosed embodiments.

Depending on the size of a room and airflow within the room, a particular shape for reflector 513 may be selected to produce an optimal distribution of intensity within the room. For example, FIG. 13 shows an example raytracing simulation of the distribution of ultraviolet light intensity over a side wall of a room obtained using different reflectors, where the ultraviolet light may be emitted from ultraviolet light sources placed in housing 515 of fixture 505. The ultraviolet radiation intensity (URI) as measured along a surface perpendicular to a ceiling (e.g., one of the side walls) may be smaller for a reference reflector 1311, as compared to a straight reflector 1312, and case 1313 where light fixture 505 has no reflector. However, some of the URI may be directed towards a ceiling, as shown, for example, in FIG. 14. As shown in FIG. 14, reflector 1311 redirects URI towards the upper volume of the room. In an example embodiment, for reflector 1311, there are two sections, 1411A and 1411B, in which the URI is the highest. Such sections may be sections of air volume in which air is thoroughly disinfected. The air from these air sections may be directed by air controlling elements 811A and 811B (shown in FIG. 8A) towards volume 822, as shown in FIG. 8B. Note that for the case of reflector 1312 and no reflector case 1313, most of the URI is distributed sideways and the URI is not significantly redirected towards a ceiling of the room. For reflector 1312 and no reflector case 1313, only small regions 1411A and 1411B are observed of relatively low intensity (e.g., URI in regions 1411A and 1411B is about twice as large for reflector 1311 as for other reflector cases 1312 and 1313). As shown in FIG. 15, reflector 1311 ensures that URI is distributed into an upper portion of a room, while for reflector 1312 and no reflector (case 1313), at least some of the URI can be found in a lower portion of the room possibly endangering people located in that portion of the room.

Figure 16:
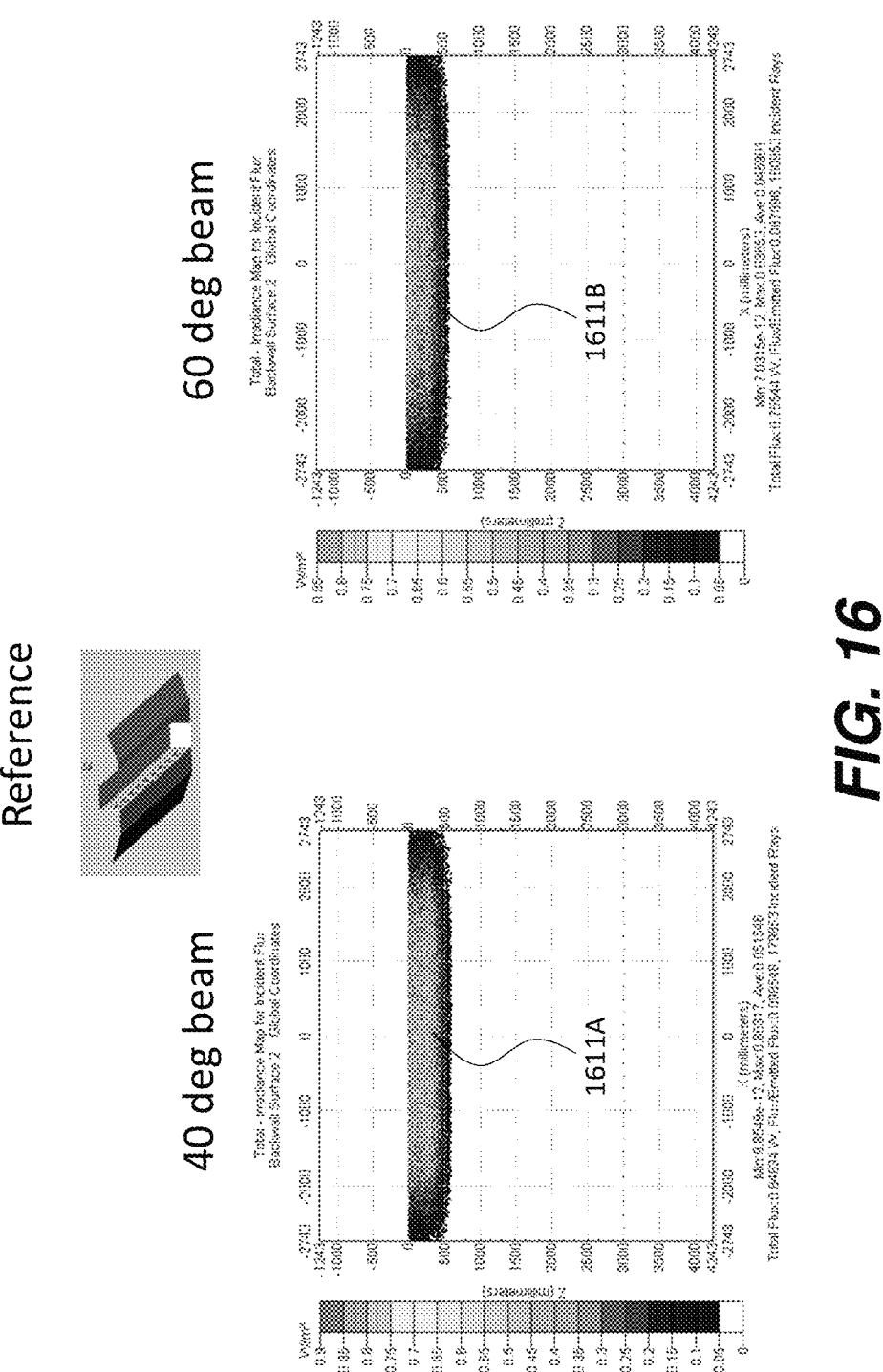
FIG. 16 is an example distribution of ultraviolet light intensity over a side wall of a room obtained for ultraviolet light sources with different angular distribution of light intensity, consistent with disclosed embodiments.
Figure 17:
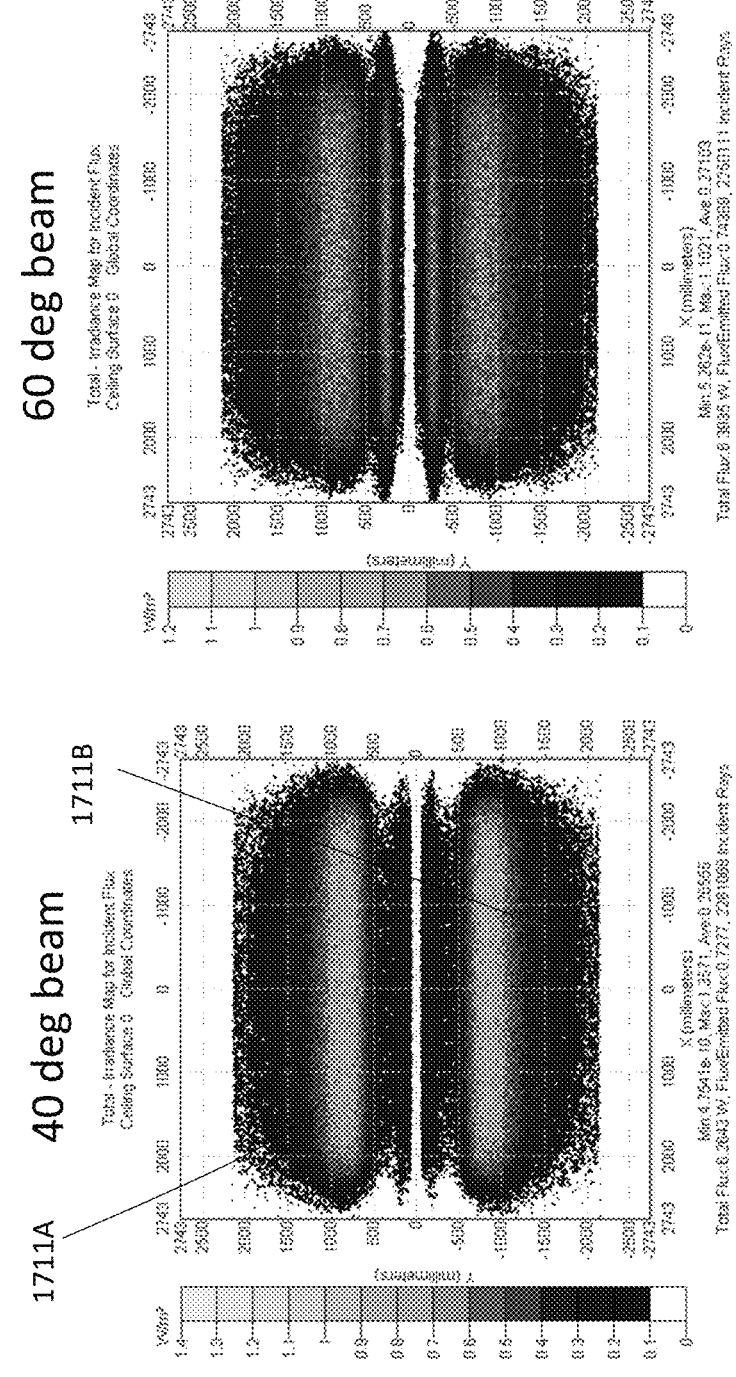
FIG. 17 is an example distribution of ultraviolet light intensity over a ceiling of a room obtained for ultraviolet light sources with different angular distribution of light intensity, consistent with disclosed embodiments.

FIGS. 16 and 17 show example distributions of ultraviolet light intensity correspondingly over a side wall of a room and a ceiling of the room obtained for ultraviolet light sources with different angular distribution of light intensity, consistent with disclosed embodiments. The distributions were obtained for a reference reflector 1311. For example, for ultraviolet light sources having an angular distribution of intensity with $\Phi_m=40°$ ($\Phi_m$, is shown in FIG. 5B), a significant amount of URI may be emitted sideways to housing 515 as indicated by region 1611A. For the ultraviolet light sourced (e.g., 510A and 510B, as shown in FIG. 5A) with $O_m=60°$, region 1611B (corresponding to region 1611A) may be significantly smaller, as shown on an intensity distribution plot corresponding to a 60-degree beam angle, as shown in FIG. 16. FIG. 17 shows the distribution of URI over a ceiling of a room obtained for ultraviolet light sources with different angular distribution of light intensity. For a 40-degree beam angle, the URI distribution includes high-intensity zones 1711A and 1711B, while for the 60-degree beam angle, the URI is more evenly distributed over a volume above light fixture 505.

In some embodiments, depending on airflow, it may be preferred to have high-intensity regions for air disinfection (e.g., region 1711A and 1711B (FIG. 17), or 1411A and 1411B (FIG. 14)). For example, when there is airflow from the upper portion of the room (e.g., from volume 821) to a lower portion of the room (e.g., to volume 822), such regions of high intensity may be preferred. Alternatively, when there is no or little airflow in the room, a more homogeneous distribution of the intensity may be preferred.

Figure 18:
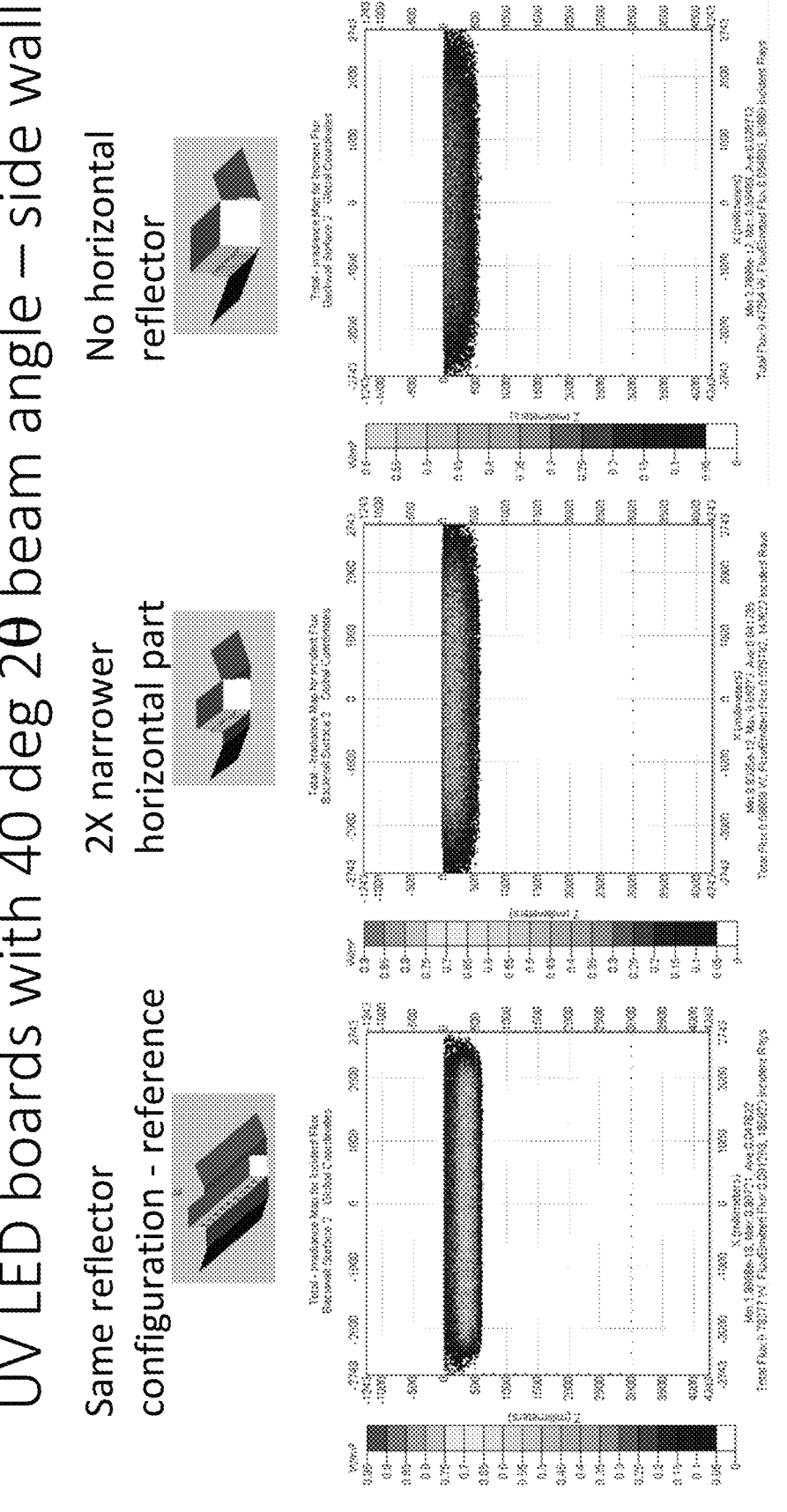
FIG. 18 shows an example distribution of ultraviolet light intensity over various surfaces, where the ultraviolet light is emitted by ultraviolet light sources with different angular distribution of light intensity, consistent with disclosed embodiments.
Figure 19:
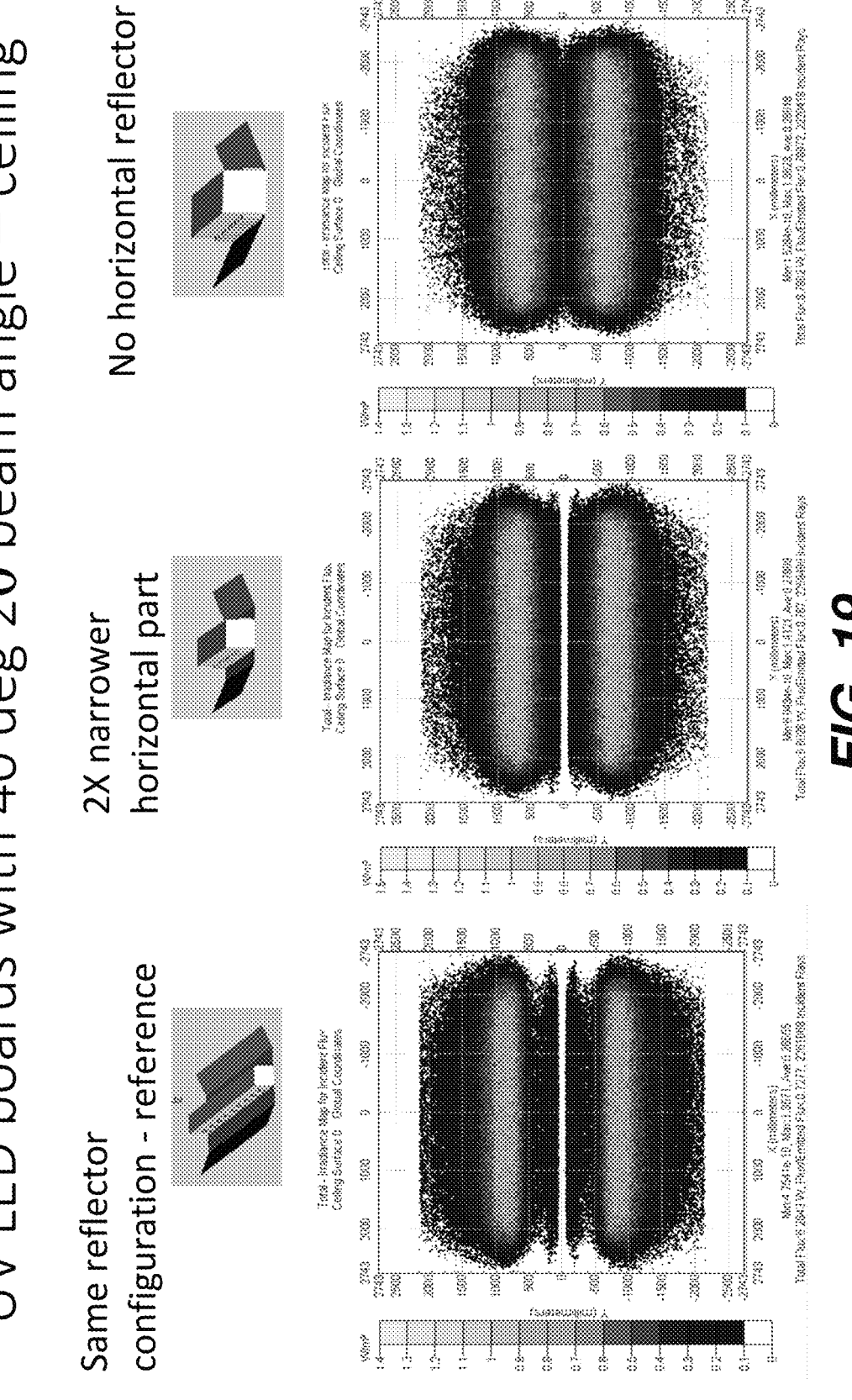
FIG. 19 shows another example distribution of ultraviolet light intensity over various surfaces, where the ultraviolet light is emitted by ultraviolet light sources with different angular distribution of light intensity, consistent with disclosed embodiments.
Figure 20:
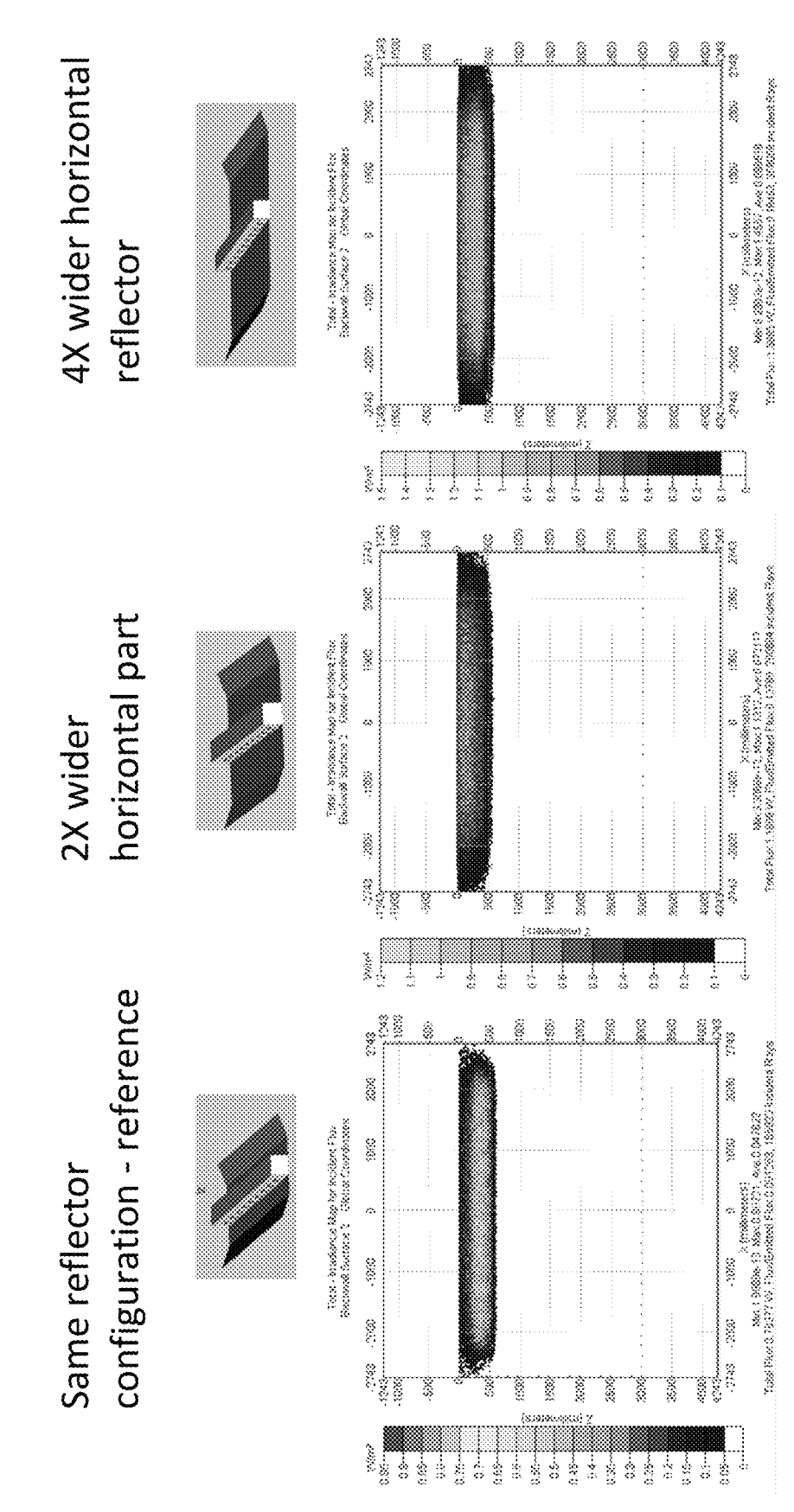
FIG. 20 shows another example distribution of ultraviolet light intensity over various surfaces, where the ultraviolet light is emitted by ultraviolet light sources with different angular distribution of light intensity, consistent with disclosed embodiments.
Figure 21:
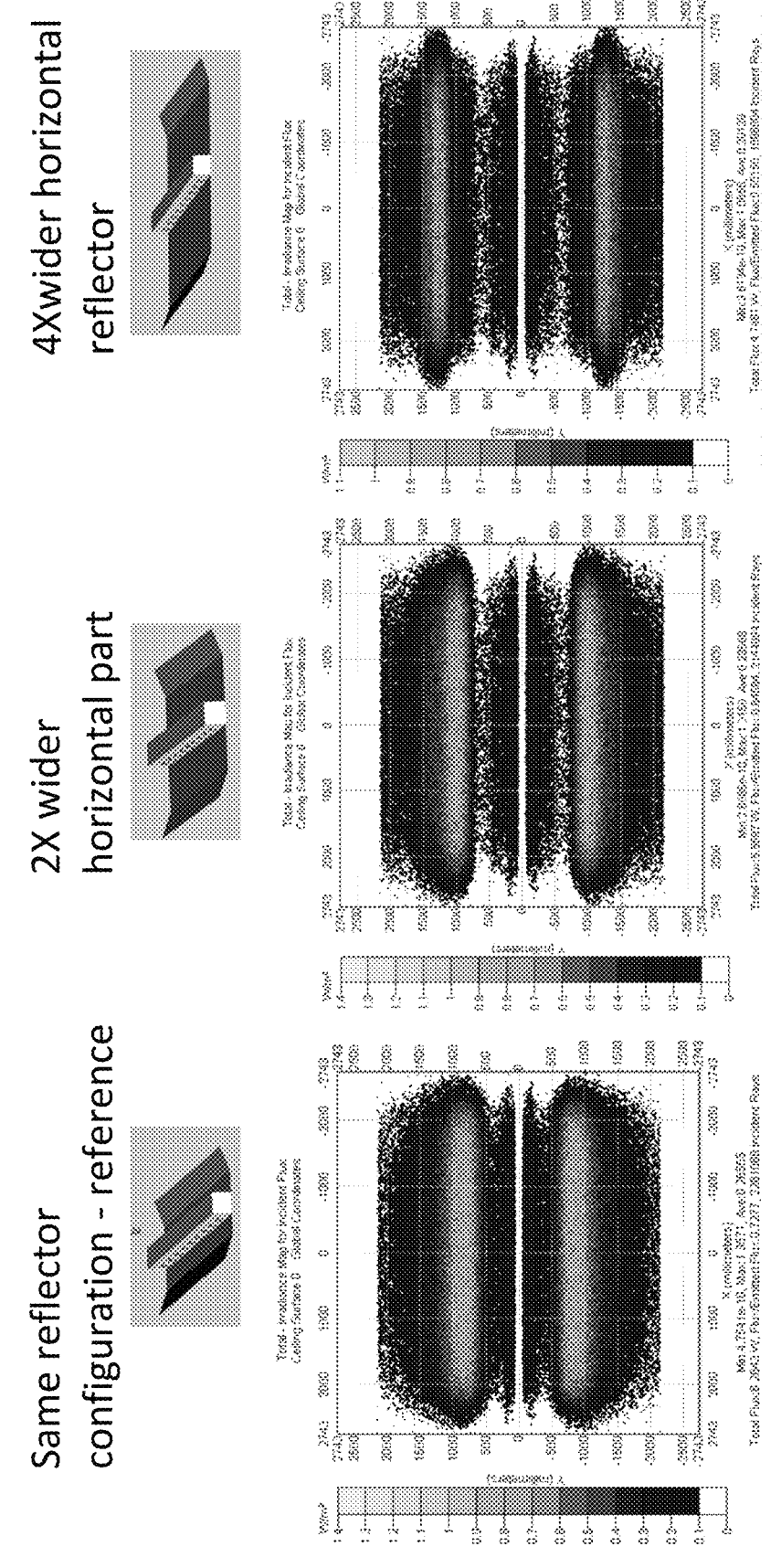
FIG. 21 shows another example distribution of ultraviolet light intensity over various surfaces, where the ultraviolet light is emitted by ultraviolet light sources with different angular distribution of light intensity, consistent with disclosed embodiments.
Figure 23:
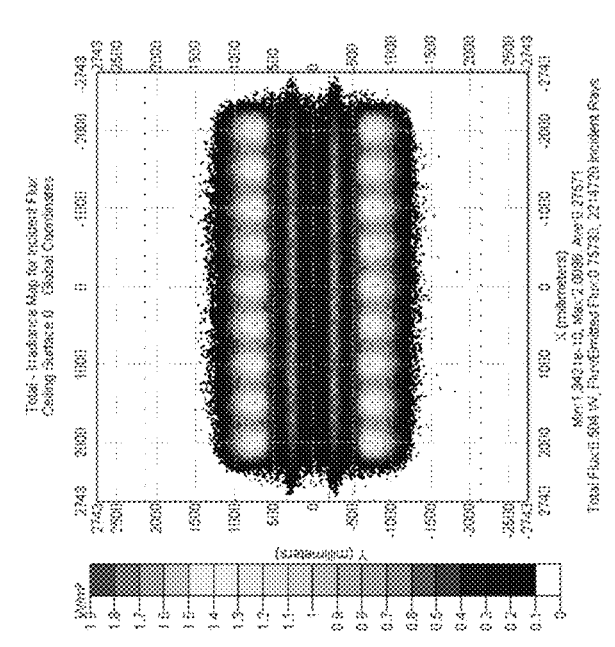
FIG. 23 shows another example distribution of ultraviolet light intensity over various surfaces, where the ultraviolet light is emitted by ultraviolet light sources with different angular distribution of light intensity, consistent with disclosed embodiments.
Figure 23:
Figure 23:
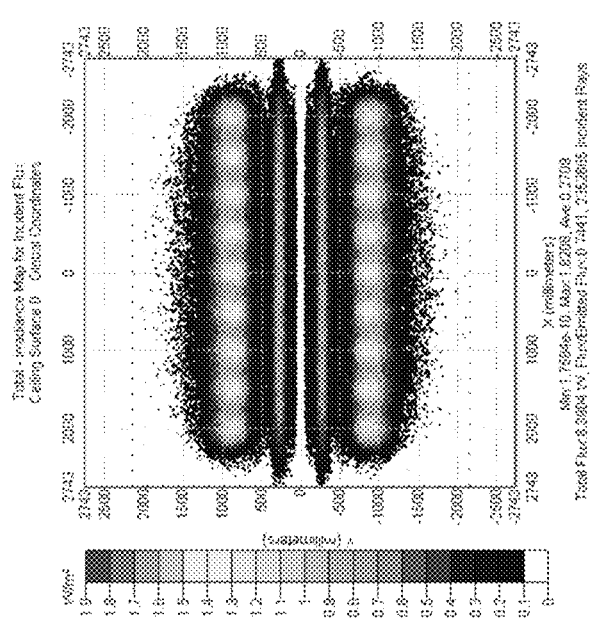
Figure 24:
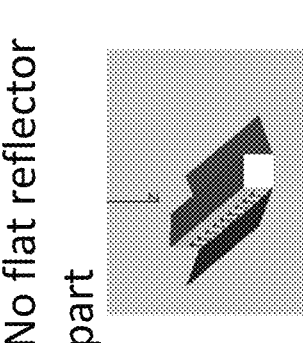
FIG. 24 shows another example distribution of ultraviolet light intensity over various surfaces, where the ultraviolet light is emitted by ultraviolet light sources with different angular distribution of light intensity, consistent with disclosed embodiments.
Figure 24:
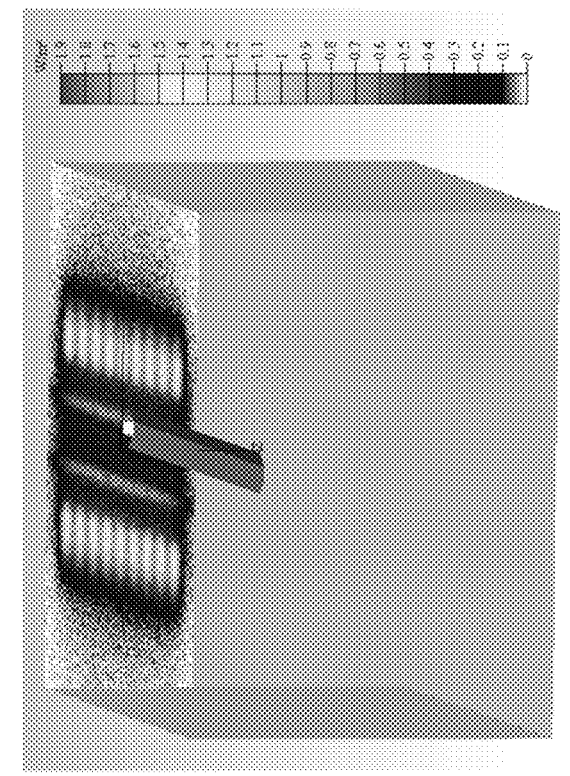
Figure 24:
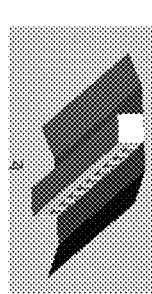
Figure 24:
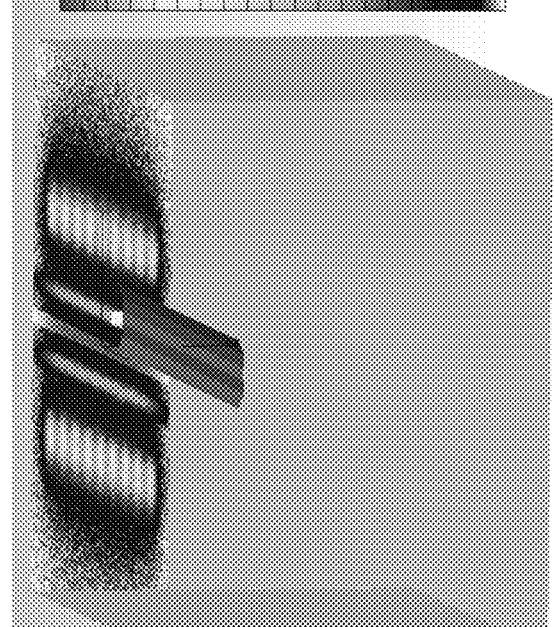
Figure 25:
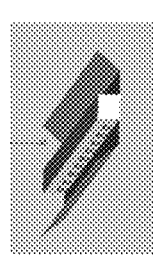
FIG. 25 shows another example distribution of ultraviolet light intensity over various surfaces, where the ultraviolet light is emitted by ultraviolet light sources with different angular distribution of light intensity, consistent with disclosed embodiments.
Figure 25:
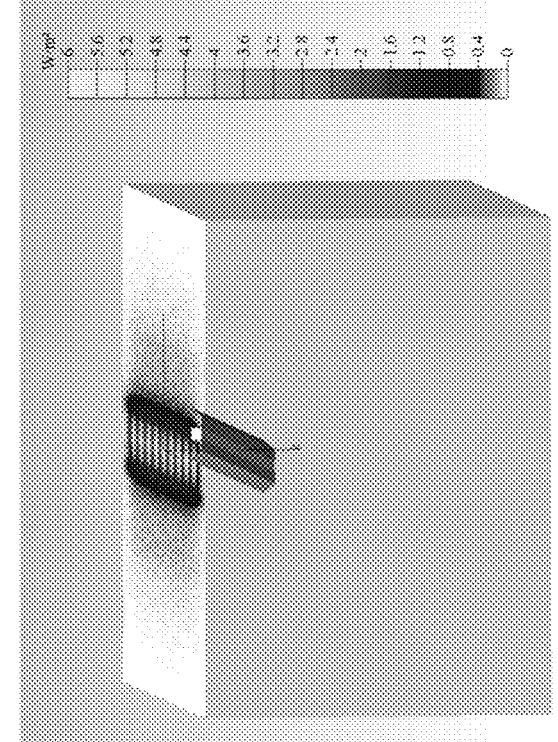
Figure 25:
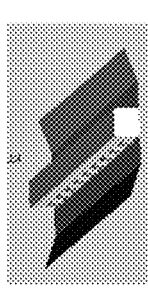
Figure 25:
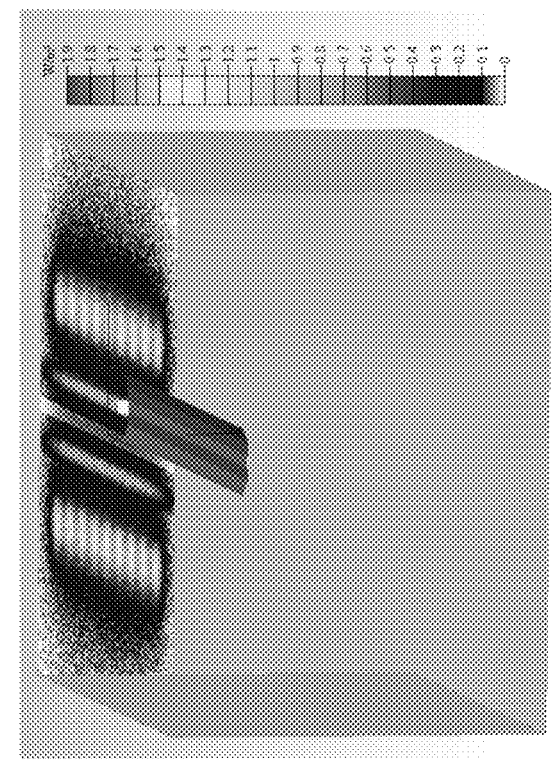
Figure 26:
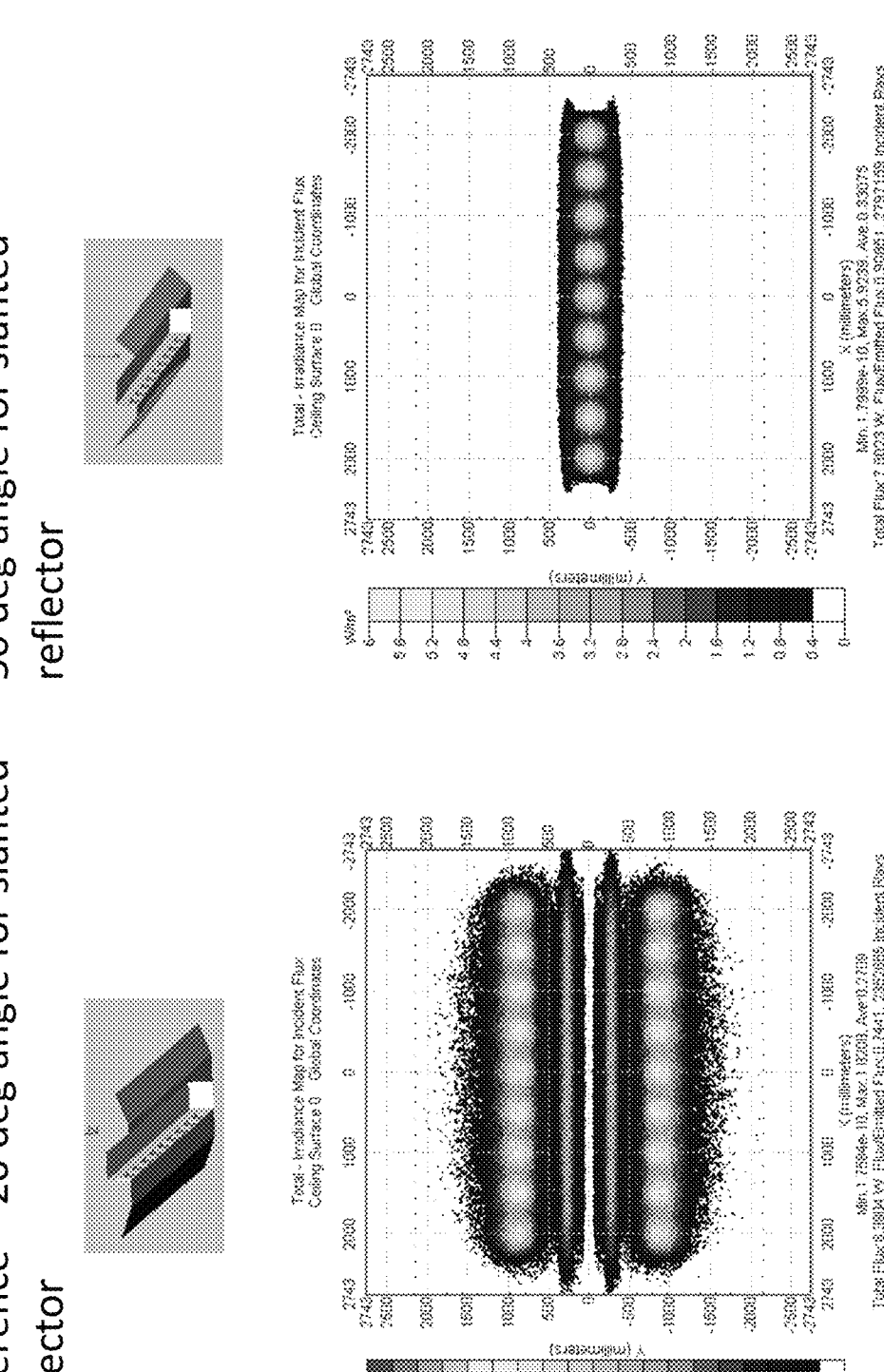
FIG. 26 shows another example distribution of ultraviolet light intensity over various surfaces, where the ultraviolet light is emitted by ultraviolet light sources with different angular distribution of light intensity, consistent with disclosed embodiments.
Figure 27:
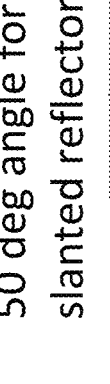
FIG. 27 shows another example distribution of ultraviolet light intensity over various surfaces, where the ultraviolet light is emitted by ultraviolet light sources with different angular distribution of light intensity, consistent with disclosed embodiments.
Figure 27:
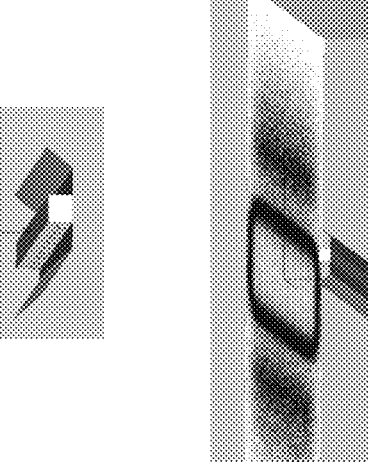
Figure 27:
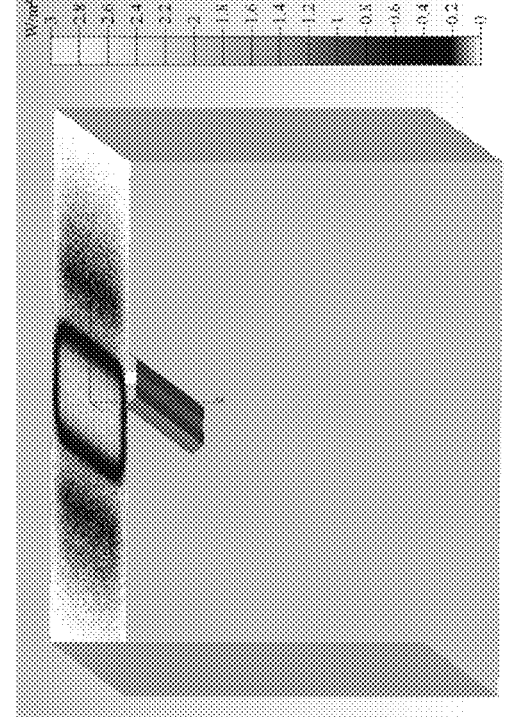
Figure 27:
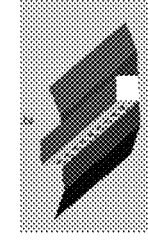
Figure 27:
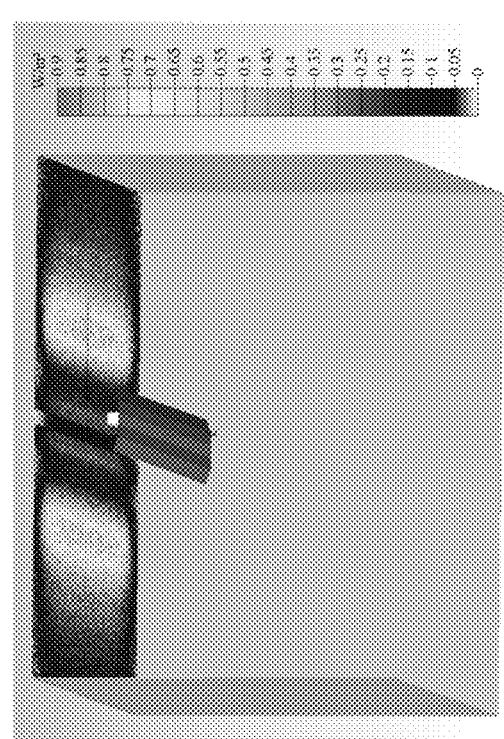
Figure 28:
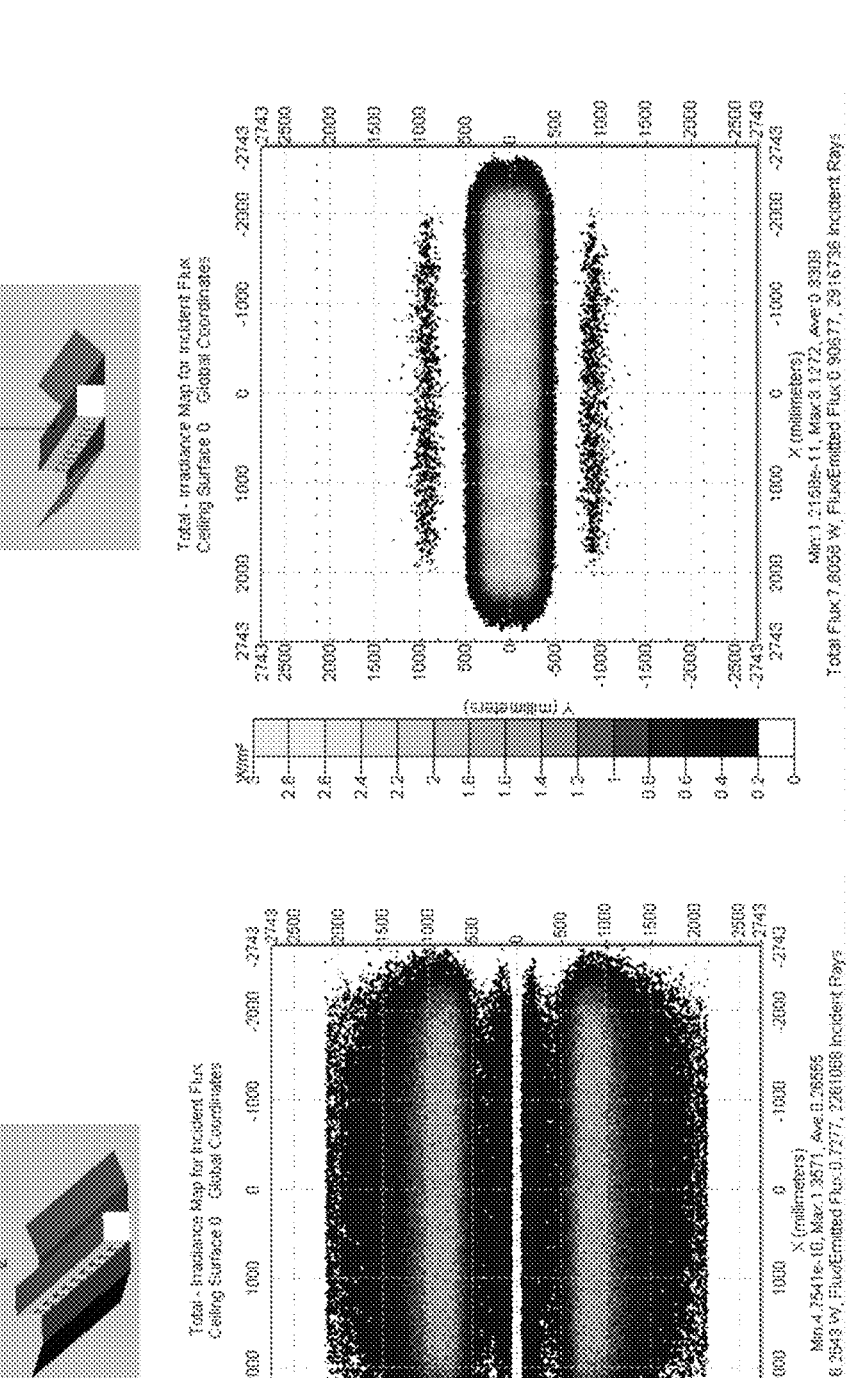
FIG. 28 shows another example distribution of ultraviolet light intensity over various surfaces, where the ultraviolet light is emitted by ultraviolet light sources with different angular distribution of light intensity, consistent with disclosed embodiments.
Figure 29:
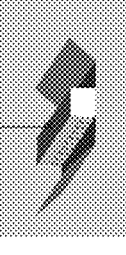
FIG. 29 shows another example distribution of ultraviolet light intensity over various surfaces, where the ultraviolet light is emitted by ultraviolet light sources with different angular distribution of light intensity, consistent with disclosed embodiments.
Figure 29:
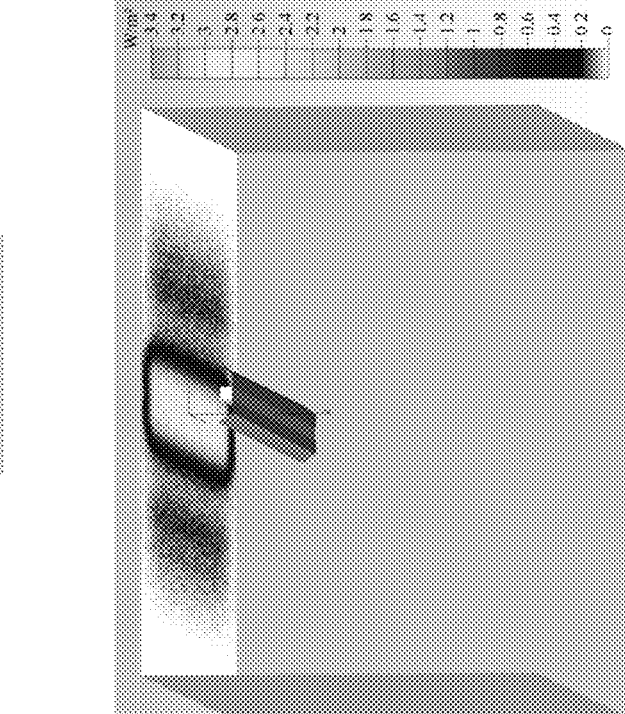
Figure 29:
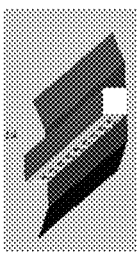
Figure 29:
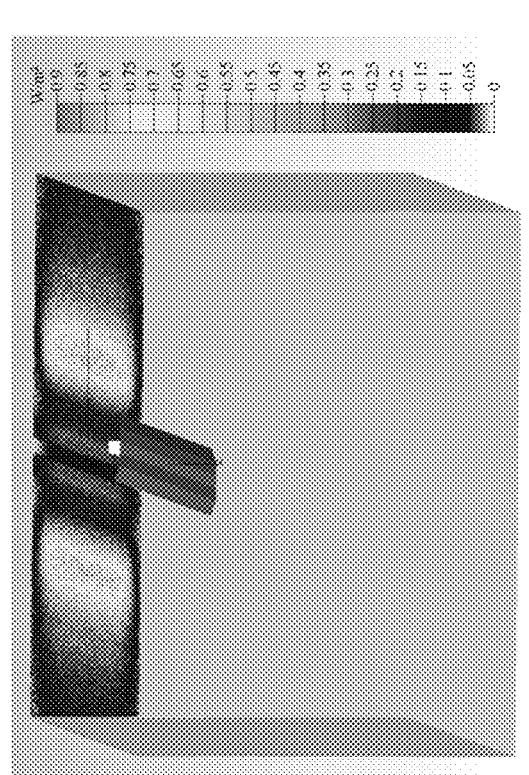
Figure 30:
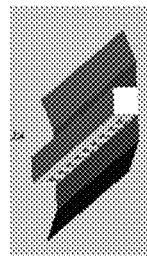
FIG. 30 shows another example distribution of ultraviolet light intensity over various surfaces, where the ultraviolet light is emitted by ultraviolet light sources with different angular distribution of light intensity, consistent with disclosed embodiments.
Figure 30:
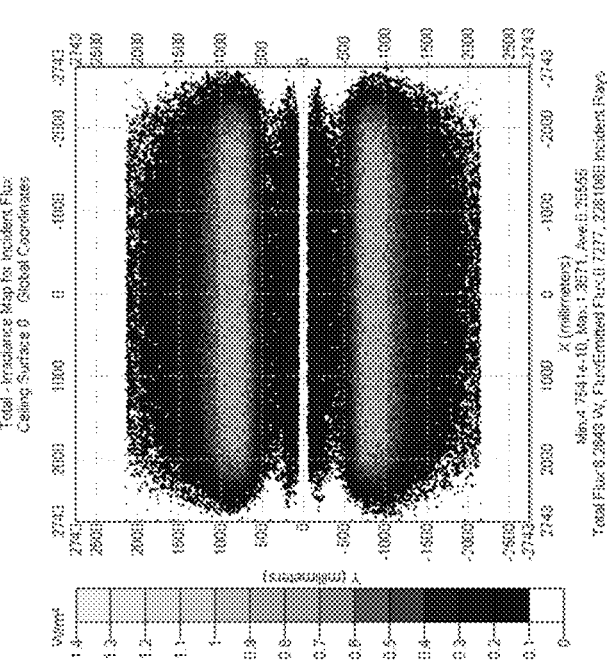
Figure 31:
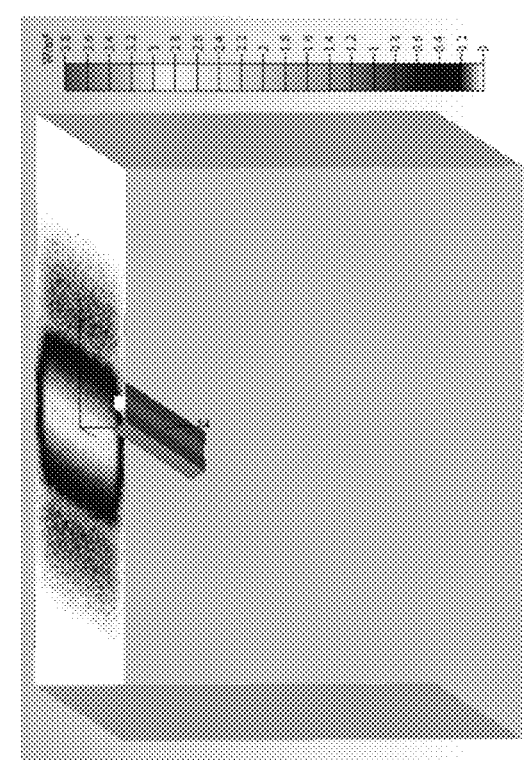
FIG. 31 shows another example distribution of ultraviolet light intensity over various surfaces, where the ultraviolet light is emitted by ultraviolet light sources with different angular distribution of light intensity, consistent with disclosed embodiments.
Figure 31:
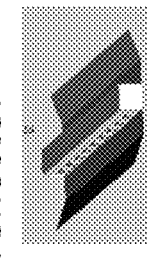
Figure 31:
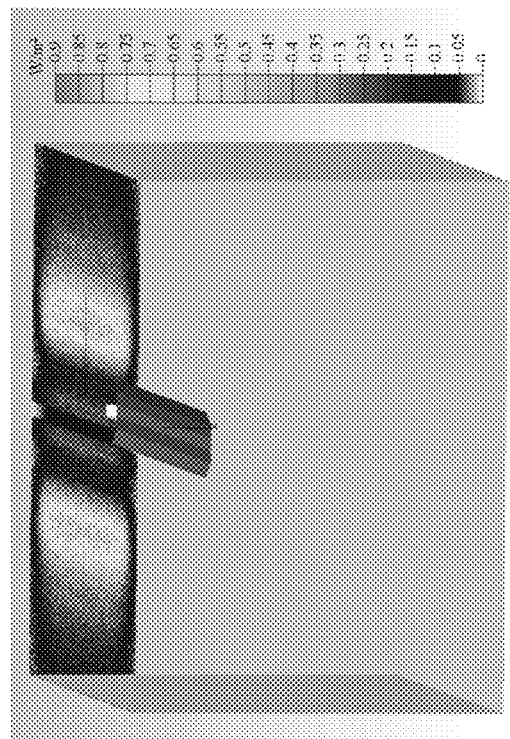
Figure 32:
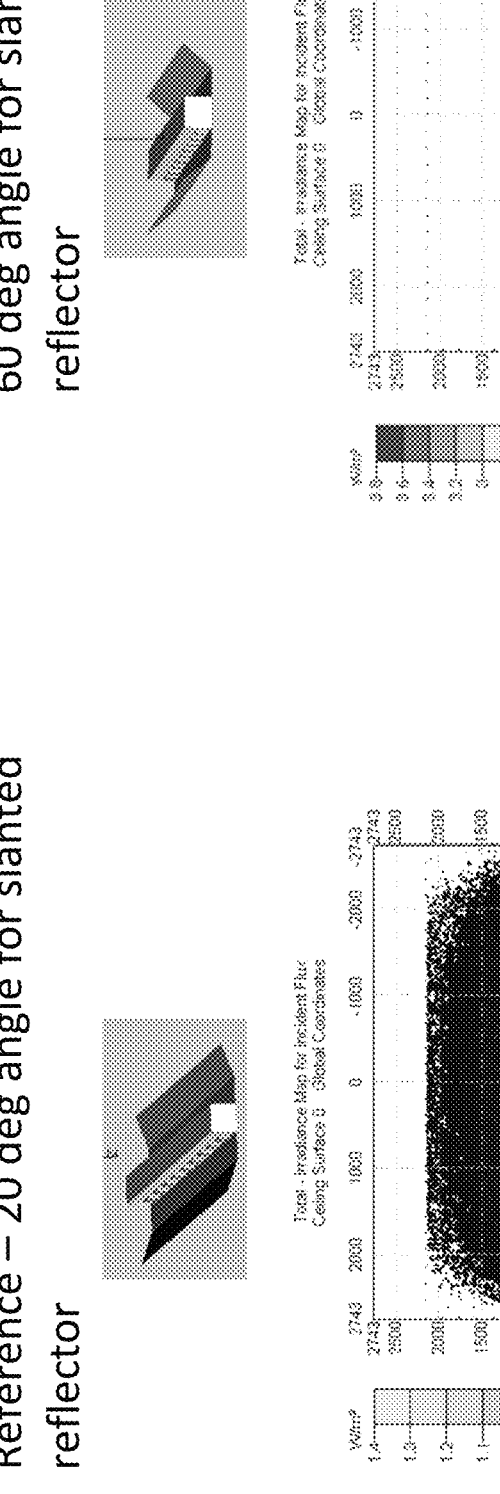
FIG. 32 shows another example distribution of ultraviolet light intensity over various surfaces, where the ultraviolet light is emitted by ultraviolet light sources with different angular distribution of light intensity, consistent with disclosed embodiments.
Figure 32:
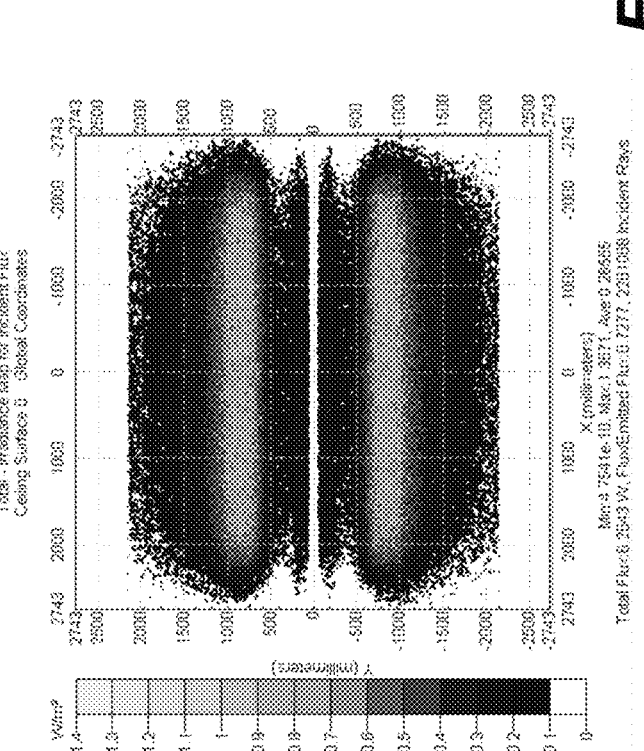
Figure 33:
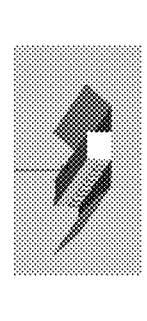
FIG. 33 shows another example distribution of ultraviolet light intensity over various surfaces, where the ultraviolet light is emitted by ultraviolet light sources with different angular distribution of light intensity, consistent with disclosed embodiments.
Figure 33:
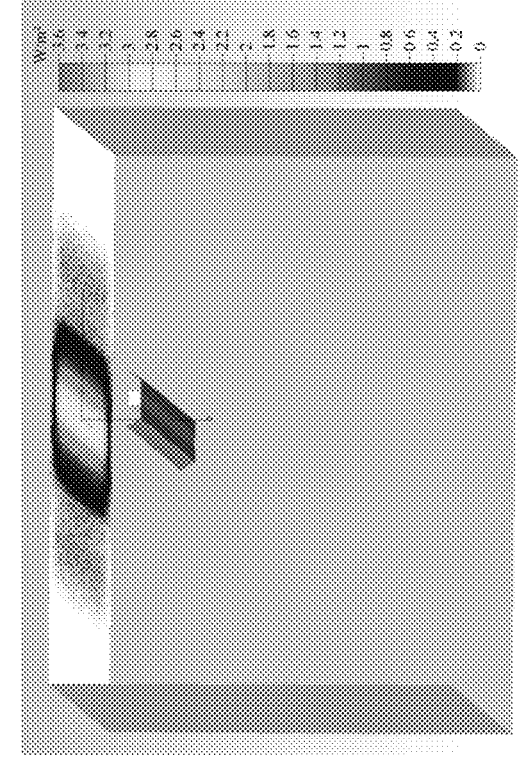
Figure 33:
Figure 33:
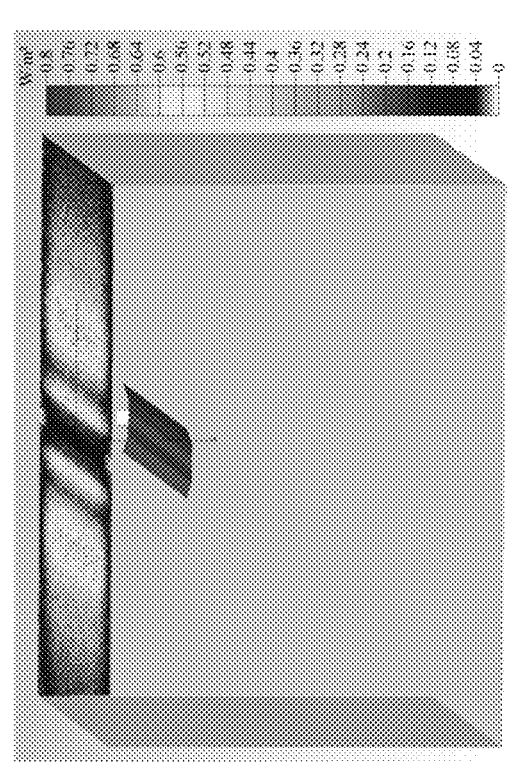
Figure 33:
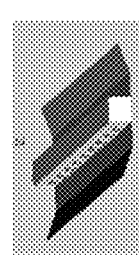
Figure 34:
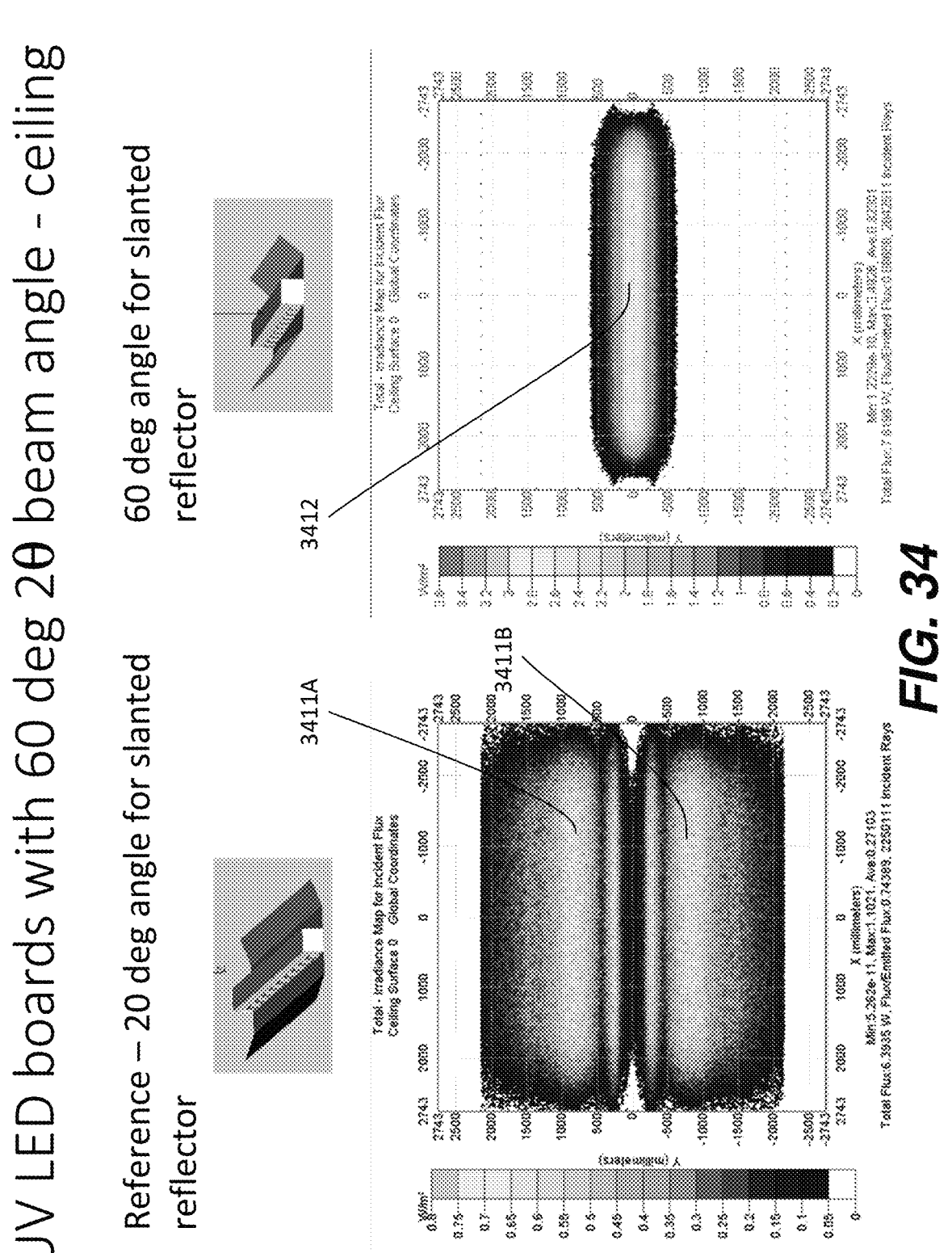
FIG. 34 shows another example distribution of ultraviolet light intensity over various surfaces, where the ultraviolet light is emitted by ultraviolet light sources with different angular distribution of light intensity, consistent with disclosed embodiments.

FIGS. 18-34 show other distributions of ultraviolet radiation intensity over different surfaces in a room. For example, FIGS. 18, 20, and 22 show a distribution of ultraviolet radiation over the walls of a room, while FIGS. 19, 21, 23-34 show a distribution of ultraviolet radiation over the ceiling of the room. In various embodiments, the distribution depends on a type of reflector, as indicated in FIGS. 18-34, and the angular distribution of radiation intensity (ADRI) emitted by ultraviolet radiation sources (e.g., 510A and 510B, as shown in FIG. 5A). In an example embodiment, a configuration of reflector and ADRI may be selected to control the location and size of high-intensity regions (e.g., region 3411A, as shown in FIG. 34). For example, for reflector 513, as shown in FIG. 34 (60-degree angle for the slanted reflector), and ADRI characterized by the angle $\Phi_m=60$, a single high intensity region 3412 is shown in FIG. 34, while for reflector (20-degree angle for slanted reflector, FIG. 34) and ADRI characterized by angle $\Phi_m=60$, two high intensity regions 3411A and 3411B are shown.

As described above, light fixture 505 or a system associated with light fixture 505 may include a control module for controlling various aspects of the operation of fixture 505. In an example embodiment, the control module may be configured to turn the UV LEDs off when an object is detected in an upper portion of the room. Such detection may be determined by proximity sensors or any other object detection sensors known in the art. These sensors may be installed on light fixture 505 or may be installed elsewhere in the room. In some cases, the control system may control more than one light fixture 505 that may be installed in a room. For example, the control system may be placed in a room remote from any of light fixtures 505. The control system may communicate with light fixture 505 using any suitable means such as wired or wireless connections. The control system may be configured to adjust URI above light fixtures 505 to result in overall target levels of URI above light fixtures 505. Furthermore, the control system may adjust the airflow rate in the room by adjusting air controlling elements 811A and 811B of fixtures 505.

In various embodiments, the control system may include human presence sensors that may be used to detect the presence of people within a room (such presence sensors are referred to herein also as proximity sensors and may include optical sensors, infrared sensors, ultrasound sensors, sensors for detecting fluctuation of light, or any other suitable sensors capable of detecting a presence of a person). If the presence of people is detected, the control system may be configured to modulate ultraviolet radiation sources (URS)

(e.g., turn off URSs to prevent irradiation of people with the UV light from URS, decrease the intensity of URS, and the like). In some cases, presence sensors may be installed elsewhere (i.e., not within light fixture 505). For example, a presence sensor may be installed above light fixture 505 (e.g., on a ceiling). In various embodiments, at least one occupancy sensor, motion sensor, proximity sensor, and the like may be incorporated in light fixture 105 and may be electrically connected to the control system that may control at least one ultraviolet radiation source. In some cases, a suitable intensity monitoring sensor(s) (e.g., a fluorescent sensor) may be used to determine the intensity of irradiation over a surface. The control system may be configured to control one or more URSs (e.g., all of the available URSs), as well as occupancy sensors, motion sensors, proximity sensors, and the like, and a power supply. In an example embodiment, the control system may control ultraviolet radiation generated by the at least one ultraviolet radiation source based on the data obtained from motion sensors or intensity monitoring sensor(s). Based on received data from intensity monitoring sensor(s), the control system may adjust the intensity of various ultraviolet radiating sources (e.g., UV LEDs) to deliver targeted ultraviolet radiation to at least one designated zone within the disinfected area (e.g., a particular portion of a volume of air in an upper room region). In some cases, when UV LEDs (or other sources of UV radiation) are movable, the control system may adjust the orientation (and/or position) of these sources to deliver targeted ultraviolet radiation to at least one designated zone within the disinfected area.

In various embodiments, light fixture 505 may have at least one electrical connection. For example, the electrical connection may follow suspension members 511A and 511B. Such an electrical connection may provide a connection not only to ultraviolet light emitting sources but also to various sensors, controllers of the control system described above, and the like. Additionally, the data connection may be used for controlling various aspects of the operation of URSs. The electrical connection may be used to power light fixture 505. In some cases, light fixture 505 may include a protective element for controlling aspects of the supplied power (e.g., the protective element may include a surge protector, a fuse, an AC-DC converter, and the like). URS may include UV LEDs electrically connected to a rectangular printed circuit board, of UV LEDs may be mounted on a flexible printed circuit board. The printed circuit board may include electrical wiring for delivering electrical power to UV LEDs.

Figure 35:
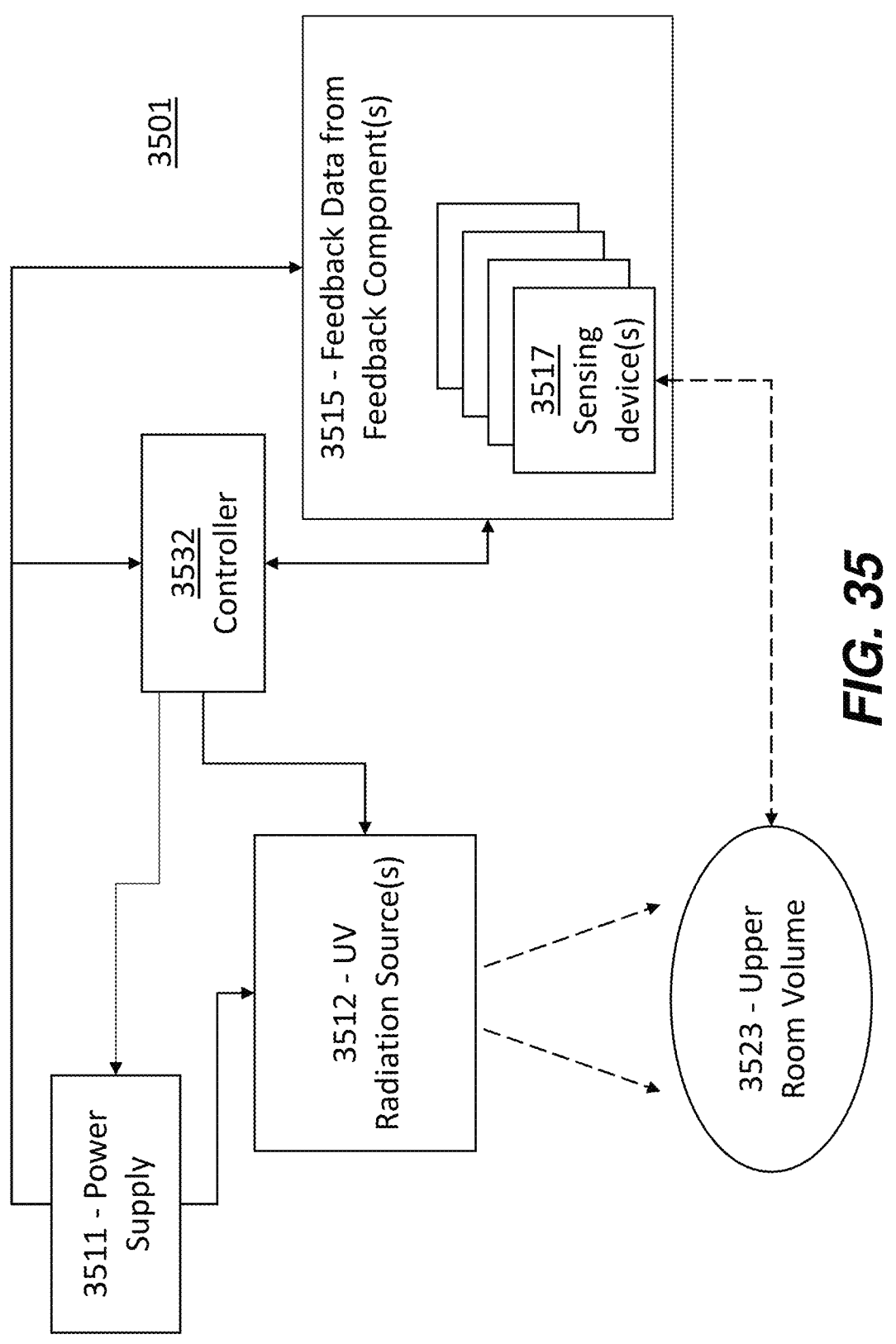
FIG. 35 shows a block/flow diagram describing a system and method of controlling various aspects of UV light emitted by ultraviolet radiation sources, consistent with disclosed embodiments.

As previously described and referring to FIG. 35, ultraviolet light emitting sources of fixture 505 may be controlled by a control system (herein, also referred to as a controller 3532 in FIG. 35). The controller 3532 may control URSs based on data collected by various sensors (e.g., proximity sensors). FIG. 35 shows an example block diagram describing a system/process 3501 of controlling various aspects of UV light emitted by URSs (e.g., URS 510A, as shown in FIG. 5A). Controller 3532, as shown in FIG. 35, may control the amount of power from a power supply 3511, control various aspects of UV radiation sources 3512 configured to irradiate upper room volume 3523 of air requiring disinfection, and change controlling parameters based on feedback data 3515 obtained from sensing devices 3517. In an example embodiment, controller 3532 may control voltage or current provided by power supply 3511.

In an example embodiment, the amount of electrical power provided by power supply 3511 is selected to obtain a required radiational dose for volume 3523. The required dose may change depending on the time of the day, frequency of use of volume 3523, amount of time available for irradiating volume 3523, or any other suitable considerations. For example, a first dose may be used to irradiate volume 3512 while there are people in the room, and a second dose may be used to irradiate volume 3523 during nighttime (or during any longer intervals of time when people are not in the room, i.e., cannot be exposed to ultraviolet radiation). Such an approach may be adopted to ensure that people are not irradiated by ultraviolet light reflected from various surfaces (e.g., walls and a ceiling) of a room. In an example embodiment, a first dose may yield a few LOG reductions (e.g., one LOG reduction, two LOG reduction, and the like) of colony forming unit (CFU) of some pathogens, such as bacteria, or plaque forming unit (PFU) of some pathogens, such as viruses, and the like, while a second dose may yield a higher LOG reduction of pathogens. A LOG reduction is a mathematical term that is used to express the relative number of living microbes that are eliminated by disinfection. For example, a 1 LOG reduction corresponds to inactivating 90 percent of a target microbe with the microbe count being reduced by a factor of 10. The first dose may require high power and may be delivered in a relatively short interval of time (e.g., an interval of time between the use of the room). For example, the first dose may be delivered for a few seconds or a few minutes. In some cases, the first dose may be delivered in short bursts. In some cases, the delivery of the first dose may be interrupted if a person or people enters the room. In various embodiments, when volume 3523 is illuminated nonuniformly, a dose may be determined to be a minimal dose received by a region of volume 3523.

In an example embodiment, while delivering an ultraviolet radiation dose, controller 3532 may continuously receive feedback data 3515 from various feedback components such as various proximity sensors 3517 (e.g., optical proximity sensors, infrared proximity sensors, ultrasound proximity sensors, and the like) as previously discussed. When feedback data 3515 indicates that one or more persons or equipment are detected in an upper room region, controller 3532 may terminate power supply to sources 3512. Additionally, or alternatively, controller 3532 may decrease (or increase) power to sources 3512 based on the proximity of one or more persons to the upper room region.

In some cases, controller 3532 may further control other aspects of sources 3512, such as the position of sources 3512 (for a case when sources are movable), the orientation of sources 3112 (for a case when sources 3112 are capable of rotation), focusing light for sources 3112 (for cases when sources 3112 may have movable optical elements for focusing light towards volume 3123), and determination of which one of sources 3112 are turned on/off. In some cases, if sources 3512 include sources of different wavelengths, controller 3532 may control the distribution of wavelengths emitted by sources 3512 by controlling the power supply to each one of sources 3512.

Figure 36:
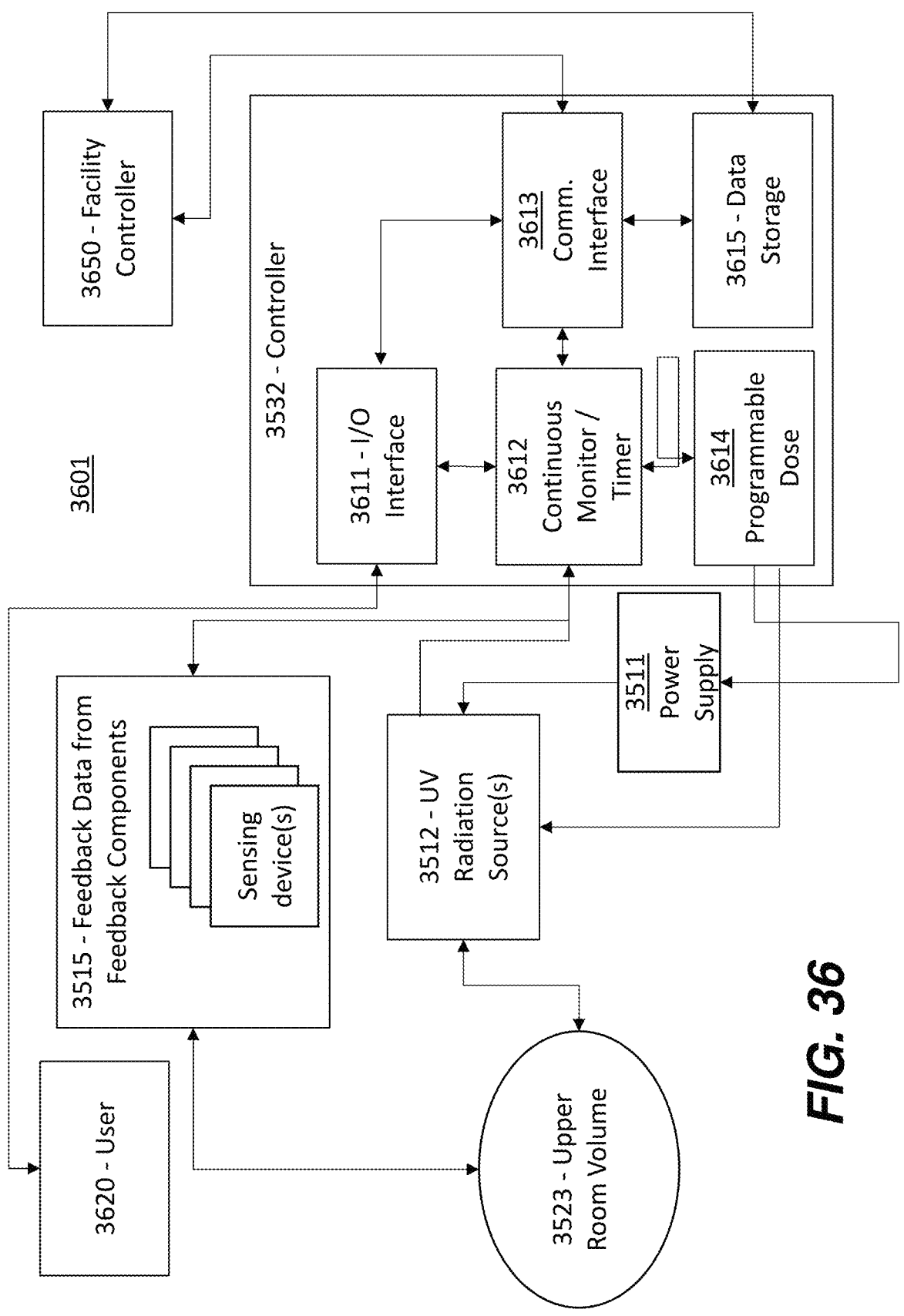
FIG. 36 shows a block/flow diagram describing a system and method of controlling irradiation of a volume of air, consistent with disclosed embodiments.

FIG. 36 shows an example block diagram describing a system and process 3601 of controlling irradiation of volume 3523. System 3601 may be a variation of system 3501, as shown in FIG. 35. Controller 3532 may be configured to control sources 3512 and receive feedback data 3515, as previously described. In various embodiments, controller 3532 may include an input/output (I/O) interface 3611 for communicating controlling parameters with a user 3620. For example, user 3620 may enter commands via I/O interface 3611 or receive various data related to the intensity of sources 3512, the performance of sources 3512, or any other suitable data related to a process of irradiating volume 3523. In an example embodiment, I/O interface 3611 may be a text or graphical interface. In an example embodiment, interface 3611 may include an application programming interface for interacting with an application installed on a device of user 3620. For example, user 3620 may monitor data received from controller 3532 on a smartphone, laptop, tablet, computer, and the like, and may enter data via a graphical interface provided by the application.

Controller 3532 may continuously monitor data 3515 via module 3612. Further, controller 3532 may control a dose of ultraviolet radiation via programmable dose module 3614. In an example embodiment, module 3614 may receive instructions on the required dose via I/O interface 3611, determine the duration of time and power levels for delivering the required dose of ultraviolet radiation to volume 3523, and, via power supply 3511, adjust power for sources 3512. In various embodiments, as previously discussed, controller 3532 may monitor feedback data 3515 regarding the presence of people/equipment in an upper room region and adjust the supplied power to ensure that the people are not exposed to the ultraviolet radiation. Additionally, controller 3532, via module 3612, may monitor the electrical performance of sources 3512 and when electrical parameters of ultraviolet radiation sources 3512 change (e.g., a resistance of a circuit related to sources 3512 changes, a current for sources 3512 changes when a power supply is a voltage supply source, voltage for sources 3512 changes when a power supply is a current source), controller 3532 may be configured to adjust power supply parameters to ensure that the required dose of radiation is delivered to volume 3523. For example, if a current delivered to sources 3512 drops (e.g., when one of UV sources 3512 malfunctions and current stops flowing through that source), controller 3532 may be configured to increase supplied voltage to increase power to sources 3512 to offset power loss due to loss of one of UV sources 3512.

Controller 3532 may implement a delay Δt for increasing the supplied voltage. Similarly, if a power supply is a current source, the current may be adjusted (increased or decreased) to result in a required dose for irradiating volume 3523, if one or more sources 3512 fail. In some cases, the performance of sources 3512 may continuously degrade with time requiring continuous adjustments for supplied power by controller 3532 in order to maintain the required dose for irradiating volume 3523. Besides adjusting power supply, controller 3532 may be configured to adjust other aspects of the operation of sources 3512. For example, as described above, if sources 3512 are movable or rotatable, controller 3532 may move or rotate sources 3512. Additionally, or alternatively, controller 3532 may control the distribution of ultraviolet light intensity over volume 3523 by turning on/off individual one of or a few sources 3512 or adjusting power to one of or a few sources 3512. Furthermore, controller 3532 may control the airflow controlling elements 811A and 811B (FIG. 8A-C). For instance, controller 3532 may control the volume of air moved by these elements. In various embodiments, sensing devices 3517 may include airflow sensors, and controller 3532 may include data obtained from such airflow sensors to adjust operations of elements 811A and 811B.

In various embodiments, controller 3532 may include a processor for processing data 3515 and electrical data from sources 3512 (e.g., voltage and current data needed to power sources 3512), and memory storage 3615 for storing various instructions related to doses for irradiating volume 3523, and for storing any other suitable data (e.g., historical data related to irradiation of volume 3523, such as historical data 3515, dates and times of when ultraviolet radiation dose was delivered to volume 3523, or any other relevant historical data). Memory storage 3615 may receive data from a communication interface 3613, where interface 3613 may be configured to collect data from module 3612, I/O interface 3611, and programmable dose module 3614. In some cases, storage 3615 may provide stored data to interface 3613. Interface 3613 may communicate with facility controller 3615 to provide various data related to irradiation of volume 3523.

In an example embodiment, facility controller 3615 may be a cloud based service that may be configured to collect data received from interface 3613. In some cases, facility controller 3615 may combine data from various sets of ultraviolet sources 3512. Furthermore, facility controller 3615 may collect data from different light fixtures 505 available within a given room (facility). For example, if a facility is a restaurant, facility controller 3615 may be configured to collect radiational data from a plurality of light fixtures 505 for the upper room region of the air. In some cases, when a facility is a medical facility, data about UV doses for different rooms, room geometries, number of fixtures 505 in a room, distances from fixtures 505 and room walls and ceiling, etc., may be transmitted to facility controller 3615 and further processed by controller 3615. In some cases, controller 3615 may be configured to display data, deliver data to different devices, and/or facilitate analysis of data.

In the foregoing specification, embodiments have been described with reference to numerous specific details that can vary from implementation to implementation. Certain adaptations and modifications of the described embodiments can be made. Other embodiments can be apparent to those skilled in the art from consideration of the specification and practice of the invention disclosed herein. It is intended that the specification and examples be considered as exemplary only, with a true scope and spirit of the invention being indicated by the following claims. It is also intended that the sequence of steps shown in figures are only for illustrative purposes and are not intended to be limited to any particular sequence of steps. As such, those skilled in the art can appreciate that these steps can be performed in a different order while implementing the same method.

The foregoing description has been presented for purposes of illustration. It is not exhaustive and is not limited to precise forms or embodiments disclosed. Modifications and adaptations of the embodiments will be apparent from a consideration of the specification and practice of the disclosed embodiments. For example, while certain components have been described as being coupled to one another, such components may be integrated with one another or distributed in any suitable fashion. The fixtures described herein may have features that are integrated in any combination. The fixtures may be employed in rooms, vehicles, aircrafts or any other volume or space.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from a consideration of the specification and practice of the embodiments disclosed herein. It is intended that the specification and examples be considered as an example only, with a true scope and spirit of the disclosed embodiments being indicated by the following claims.

What is claimed is:

1. A light fixture, comprising:
a housing forming a cavity and having an inlet to permit airflow therethrough;
a first ultraviolet (UV) light emitting diode (LED) external to the cavity to direct UV light from the first UV LED to treat the airflow prior to entering the inlet;
a filter disposed within the airflow of the cavity; and
a second UV LED disposed within the cavity, the second UV LED being directed to concurrently treat the airflow and the filter to destroy biomaterial therein.

2. The light fixture as recited in claim 1, further comprising a forced convection device to draw air into the cavity.

3. The light fixture as recited in claim 1, wherein the filter includes an ultraviolet light resistant material.

4. The light fixture as recited in claim 1, wherein the first UV LED treats the filter on an inlet side of the filter.

5. The light fixture as recited in claim 1, wherein the filter includes a plurality of filters and an intermediary ultraviolet radiation source is disposed between filters in the plurality of filters.

6. The light fixture as recited in claim 1, wherein the filter has a collection efficiency of more than 99.9% with the most penetrating particle size of less than 0.3 micron.

7. The light fixture as recited in claim 1, further comprising a reflector coupled to the housing to direct light emitted from first UV LED externally about the inlet.

8. The light fixture as recited in claim 1, further comprising a controller to control the activation of the first UV LED to protect humans and pets in an ultraviolet light avoidance area.

9. The light fixture as recited in claim 1, further comprising a controller to control airflow and an intensity of radiation, the controller including a programmable dose module to store a required radiation dose, the controller controlling power and time based on sensor feedback to ensure a UV radiation dose is achieved.

10. The light fixture as recited in claim 1, further comprising a visible light disposed on the housing.

11. The light fixture as recited in claim 1, wherein the light fixture is suspended from a ceiling.

12. A light fixture, comprising:

a housing forming a cavity and having an inlet to permit airflow therethrough;

an ultraviolet radiation source including a first ultraviolet (UV) light emitting diode (LED) external to the housing to direct UV light from the first UV LED to treat the airflow prior to entering the inlet;

a reflector being opaque to the UV light, the reflector having a reflective surface with a distant region and an adjacent region, wherein at least a portion of the adjacent region is located close to and below the ultraviolet radiation source, and the distant region is further from the ultraviolet radiation source than the adjacent region and extends to a position above the ultraviolet radiation source such that ultraviolet radiation from the ultraviolet radiation source is directed upward to treat a volume of air before entering the inlet.

13. The light fixture as recited in claim 12, further comprising a forced convection device to draw air into the cavity.

14. The light fixture as recited in claim 12, further comprising a filter disposed at the inlet of the cavity and within the volume such that the filter is exposed to the UV light during operation.

15. The light fixture as recited in claim 14, wherein the filter includes an ultraviolet light resistant material.

16. The light fixture as recited in claim 14, wherein the first UV LED is on an inlet side of the filter and a second UV LED is on an outlet side of the filter.

17. The light fixture as recited in claim 14, wherein the filter includes a plurality of filters and an intermediary ultraviolet radiation source is disposed between filters in the plurality of filters.

18. The light fixture as recited in claim 14, wherein the filter has a collection efficiency of more than 99.9% with the most penetrating particle size of less than 0.3 micron.

19. The light fixture as recited in claim 12, further comprising a visible light disposed opposite the reflective surface.

20. A light fixture, comprising:

a housing forming a cavity to permit airflow therethrough;

a forced convection device to draw air into the cavity through an inlet;

an ultraviolet light resistant filter disposed within the airflow of the cavity;

a first ultraviolet (UV) light emitting diode (LED) disposed within the cavity, the first UV LED being directed to concurrently treat the airflow and the filter to destroy biomaterial therein;

a reflector coupled to the housing to direct light emitted from a second UV LED external to the cavity to treat the airflow prior to entering the inlet; and a controller to control airflow and an intensity of radiation of the at least one light emitting diode, the controller including a programmable dose module to store a required radiation dose, the controller controlling power and time based on sensor feedback to ensure a radiation dose is achieved.

21. The light fixture as recited in claim 20, further comprising a third UV LED on an inlet side of the filter and the first UV LED on an outlet side of the filter.

22. The light fixture as recited in claim 20, wherein the filter Includes a plurality of filters and an intermediary ultraviolet radiation source is disposed between filters in the plurality of filters.

23. The light fixture as recited in claim 20, wherein the filter has a collection efficiency of more than 99.9% with the most penetrating particle size of less than 0.3 micron.

24. The light fixture as recited in claim 20, further comprising a visible light disposed on the housing.

25. The light fixture as recited in claim 20, wherein the light fixture is suspended by an element attached to the housing.

26. The light fixture as recited in claim 20, wherein the controller further controls activation of ultraviolet light to protect humans and pets in an ultraviolet light avoidance area.

\* \* \* \* \*